US006221941B1

(12) United States Patent
Strauss et al.

(10) Patent No.: US 6,221,941 B1
(45) Date of Patent: Apr. 24, 2001

(54) WEAKLY COORDINATING ANIONS CONTAINING POLYFLUOROALKOXIDE LIGANDS

(75) Inventors: Steven H. Strauss; Benjamin G. Nolan, both of Fort Collins, CO (US); Thomas J. Barbarich, Houston, TX (US); Juston J. Rockwell, Culver City, CA (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/151,852

(22) Filed: Sep. 11, 1998

Related U.S. Application Data

(60) Provisional application No. 60/058,524, filed on Sep. 11, 1997.

(51) Int. Cl.[7] .................................................... C08K 5/00

(52) U.S. Cl. ........................................... 524/176; 556/40

(58) Field of Search ............................... 524/176; 556/40

(56) References Cited

U.S. PATENT DOCUMENTS

| 5,534,370 | 7/1996 | Kita et al. | 429/198 |
| 5,660,947 | 8/1997 | Wuhr | 429/192 |

FOREIGN PATENT DOCUMENTS

| WO 96/26967 | 9/1996 | (WO) . |
| WO 00/20472 | 4/2000 | (WO) . |

OTHER PUBLICATIONS

Labrize et al; "Sythesis, Characterization . . . ", Polyhedron vol. 14; 1995; pp. 881–848.*
Barbarich, et al.; "Coordination of the new weakly coordinating anions $Al(OCH(CF_3)_2)_4^-$, and $Al(OC(Ph)(CF_3)_2)_4$–to the monovalent metal ions Li$^+$ and Tl$^-$"; Journal of Molecular Catalysis A:Chemical; v. 128; 1998; pp. 289–331.
Rockwell, et al.; "Nb $(OCH(CF_3)_2)_6^-$: protype for a new class of weakly coordinating anions based on polyfluoroalkoxide substituents", Inorg. Chemical Act. v. 263 , 1997; pp. 195–200.
Samuels, et al.; "Organofluorine Binding to Sodium and Thallium (I) in Molecular Fluoroalkoxide Compounds"; J. Am. Chem. Soc. v. 115; 1993; pp. 5093–5104.
Perozzi, et al.; "Directed Dilithiation of Hexafluorocumyl Alcohol—Formation of a Reagent for the Facile Introduction of a Stabilizing Bidentate Ligand in Compounds of Hypervalent Sulfur (10–S–4), Phosphorus (10–P–5)) Silicon (10–Si–5), and Iodine (10–I–3)"; The Journal of Organic Chemistry; v. 46; 1981; pp. 1049–1053.
Denmark, et al.; "Synthesis, Structure, and Reactivity of an Organogermanium Lewis Acid"; Organometallics v. 9, 1990; pp. 3015–3019.

Akiba, et al.; "First Example of Thermally Stable Hypervalent Bismuth Ate Complex (12–Bi–6) with Two Bidentate Ligands: Synthesis and Structure"; Tet. Lett. v. 30; 1989; pp. 953–956.
Laurent, et al.; "Synthesis and Characterization of Volatile Sodium Yttrium Fluoroalkoxides. Structure of $Na_3Y(OCH(CF_{32})_6(THF)3$ and $Na_2Y(OCMe(CF_3)_2)_5(THF)3$"; Inorg. Chem. v. 34; 1995, 34 pp. 3980–3985.
Samuels, et al.; "Structure/Volatility Correlation of Sodium and Zirconium Fluoroalkoxides"; Chem. Mater. v. 6; 1995; pp. 929–935.
Yamamoto, et al.; "Synthesis and Structure of Six–Coordinated Organobismuth Compounds with Bidentate Ligands (12–Bi–6)"; Organometallics v. 12; 1993, 3297–3303.
Samuels, et al.; "Structure/Volatility Correlation of Sodium and Zirconium Fluoroalkoxides"; Chem. Mater. v. 7; 1995; pp. 929–935.
Allan, et al.; "Fully fluorinated alkoxides. Part IV. Derivatives of perfluoropinacol"; Canadian Journal of Chemistry, v. 46; 1968; pp. 3671–3677.
Barthel, et al.; "A New Class of Electrochemically and Thermally Stable Lithium Salts for Lithium Battery Electrolytes: II. Conductivity of Lithium Organoborates in Dimethoxyethane and Propylene Carbonate"; J. Electrochem. Soc., vol. 143 1996; pp. 3565–3571.
Barthel, et al.; "A New Class of Electrochemically and Thermally Stable Lithium Salts for Lithium Batter Electrolytes: III. Synthesis and Properties of Some Lithium Organoborates"; J. Electrochem. Soc., vol. 143; 1996; pp. 3572–3575.
Lee, et al.; "The Synthesis of a New Family of Boron–Based Anion Receptors and the Study of Their Effect on Ion Pair Dissociation and Conductivity of Lithium Salts in Nonaqueous Solutions"; J. Electrochem. Soc. vol. 145; 1998; pp. 2813–2818.
Barbarich, et al.; "$LiAl(OC(Ph)CF_3)_2)_4$: A Hydrocarbon Soluble Catalyst for Carbon–Carbon Bond–Forming Reactions"; Organometallics v. 15; 1996; pp. 3776–3778.
Purdy, et al.; "New Alkoxides of Copper and the Alkaline and Alkaline–Earth Metals. Crystal Structure of $Na_2Cu(OCH(CF_3)_{2,4}$"; Inorg. Chem. v. 30; 1991; pp. 2812–2819.
Purdy and George; "Volatile Copper and Barium–Copper Alkoxides. Crystal Structure of a Tricoordinate Copper (II) Complex, $Ba(Cu(OCMe(CF_3)_2)_3)_2$"; Inorg. Chem. v. 30; pp. 1969–1970.

(List continued on next page.)

Primary Examiner—Edward J. Cain
(74) Attorney, Agent, or Firm—Townsend and Townsend and Crew LLP

(57) ABSTRACT

A compound comprising a polyfluorinated anion of the formula $[M_1(XC(CF_a(R_1)_b)(CF_c(R_2)_d)R_3)_m(R_4)_n]^{-p}$ and the use thereof is provided. Specifically, the present invention provides a compound comprising a anion which comprises a polyfluorinated alkoxide coordinated to a transition metal, or a Group III, IV or V element.

57 Claims, 7 Drawing Sheets

OTHER PUBLICATIONS

Labrize and Hubert–Pfalzgraf; "Synthesis, Characterization and Reactivity of Volatile Yttrium–Sodium Fluoroisopropoxide Derivatives. Retention of Sodium as a General Feature", *Polyhedron vol. 14*; 1995; pp. 881–888.

Purdy and George; "Recent Developments in the Chemistry of Fluorinated Isopropoxides and Tertiary Butoxides"; 1994; *Inorganic Fluorine Chemistry: Toward the 21st Centrury, Chapter 26*; pp. 405–420.

Willis; "Fluorinated Alcohols and Their Metal Complexes"; *Coordination Chemistry Reviews, v. 88*; 1988 pp. 133–202.

* cited by examiner

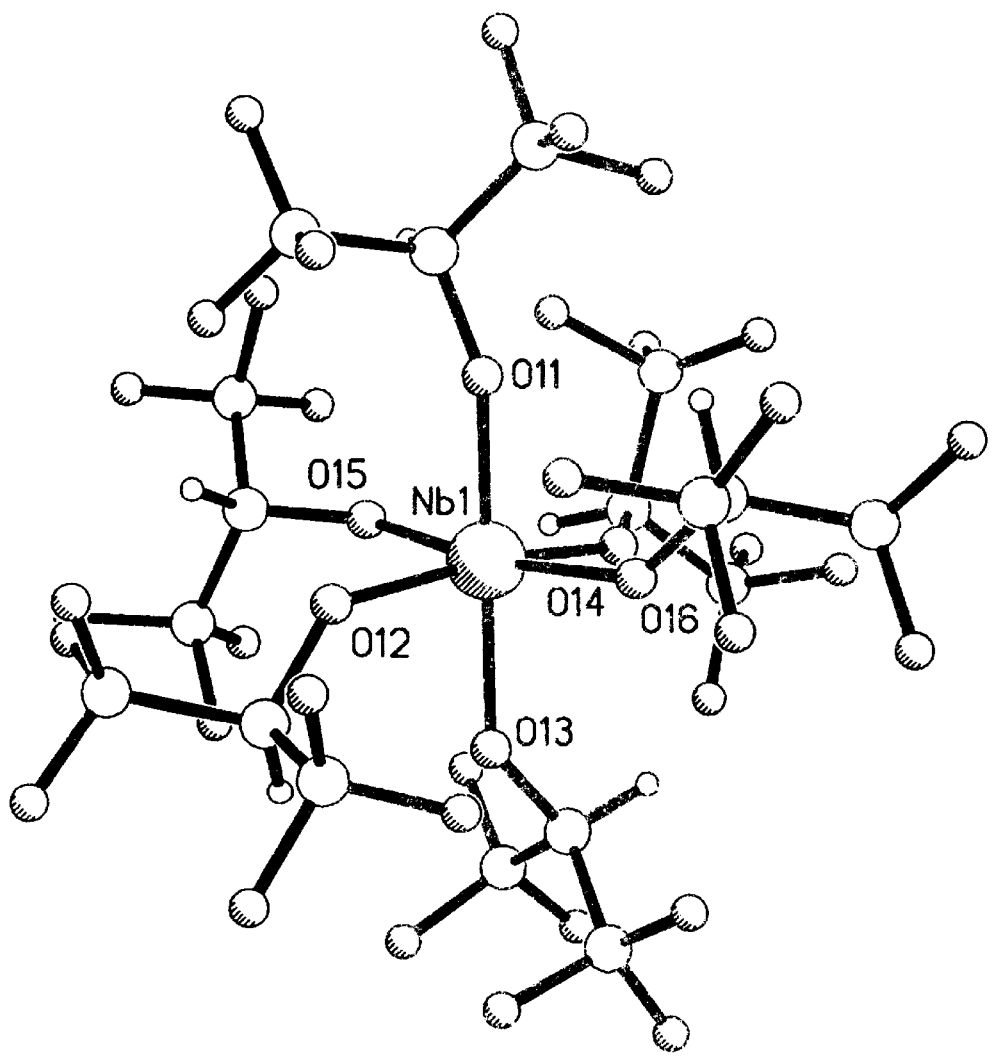
Figure 1. A ball and stick representation of one of the two $Nb(OCH(CF_3)_2)_6^-$ anions in the asymmetric unit of crystals of $[2,6-(CH_3)C_6H_4N^-][Nb(OCH(CF_3)_2)_6^-]$. The larger unlabeled open circles are carbon atoms. The smaller unlabeled open circles are hydrogen atoms. The unlabeled shaded circles are fluorine atoms. The Nb–O distances range from 1.929(8) to 1.998(8) Å.

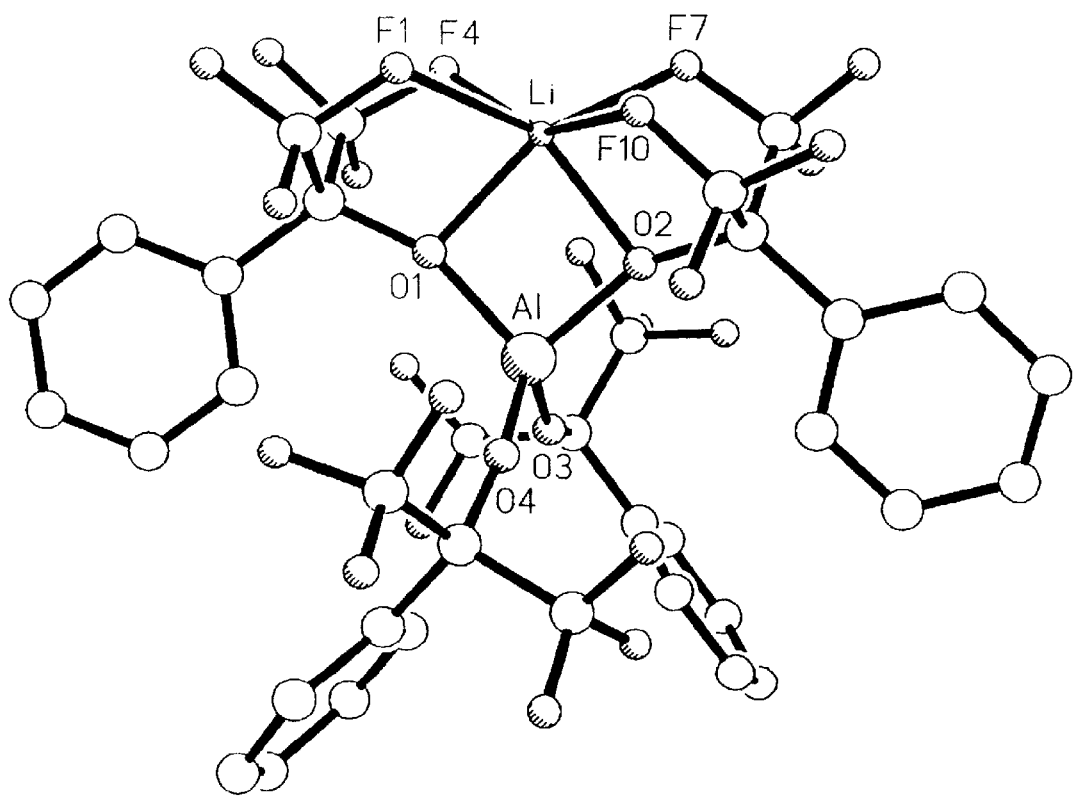
Figure 2. Drawing of the structure of $LiAl(OC(C_6H_5)(CF_3)_2)_4$ (hydrogen atoms omitted for clarity). The unlabeled shaded circles are fluorine atoms, while the unlabeled open circles are carbon atoms. Selected interatomic distances (Å) and angles (deg): Li–O1, 1.978(8); Li–O2, 1.966(8); Li–F1, 1.984(9); Li–F4, 2.354(10); Li–F7, 2.098(11); Li–F10, 2.082(9); O1–Li–O2, 79.9(3).

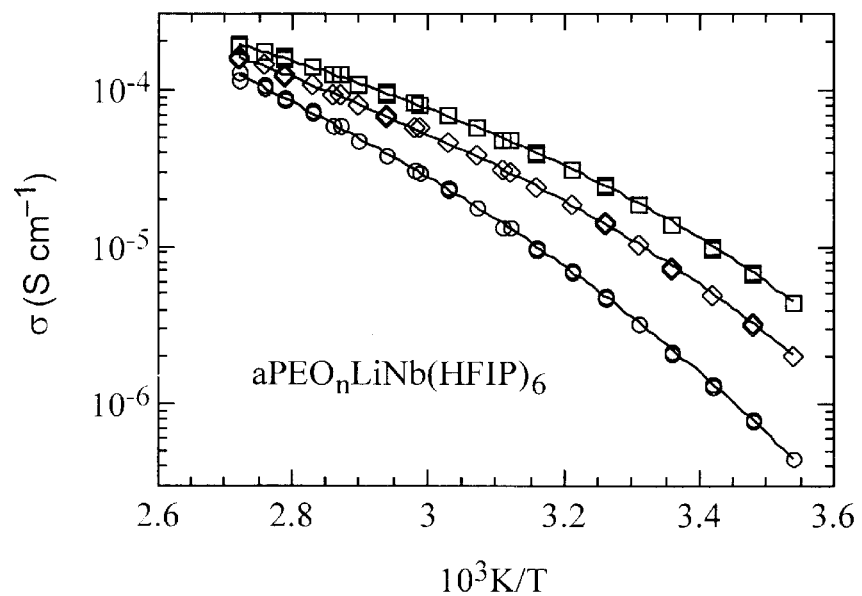
Figure 3. D.c. conductivity vs. 1/T plots for the three solid polymer electrolytes made with amorphous polyethylene oxide and $LiNb(HFIP)_6$ (HFIP = $OCH(CF_3)_2$) (circles, n = 12; squares, n = 24; diamonds, n = 30). The solid lines through the data points are least-squares fits of the data to the VTF equation.

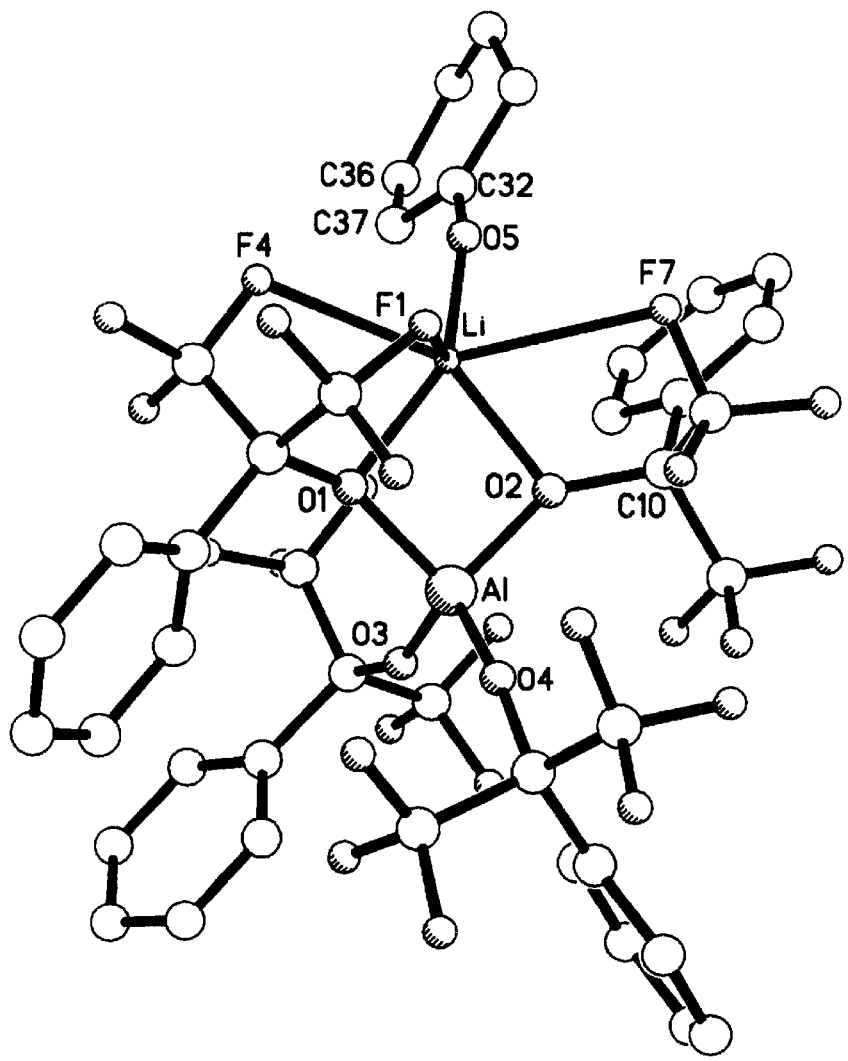
Figure 4. Drawing of the structure of $LiAl(OC(Ph)(CF_3)_2)_4$ with coordinated 2-cyclohexen-1-one (hydrogen atoms omitted for clarity). The unlabeled shaded circles are fluorine atoms, while the unlabeled open circles are carbon atoms. Selected interatomic distances (Å) and angles (deg): Li–O1, 2.028(9); Li–O2, 2.02(1); Li–O5, 1.830(9); Li–F1, 2.27(1); Li–F4, 2.48(1); Li–F7, 2.75(1); O5–C32, 1.230(6); O1–Li–O2, 78.1(3); O1–Al–O2, 92.1(2); Li–O5–C32, 154.1(6).

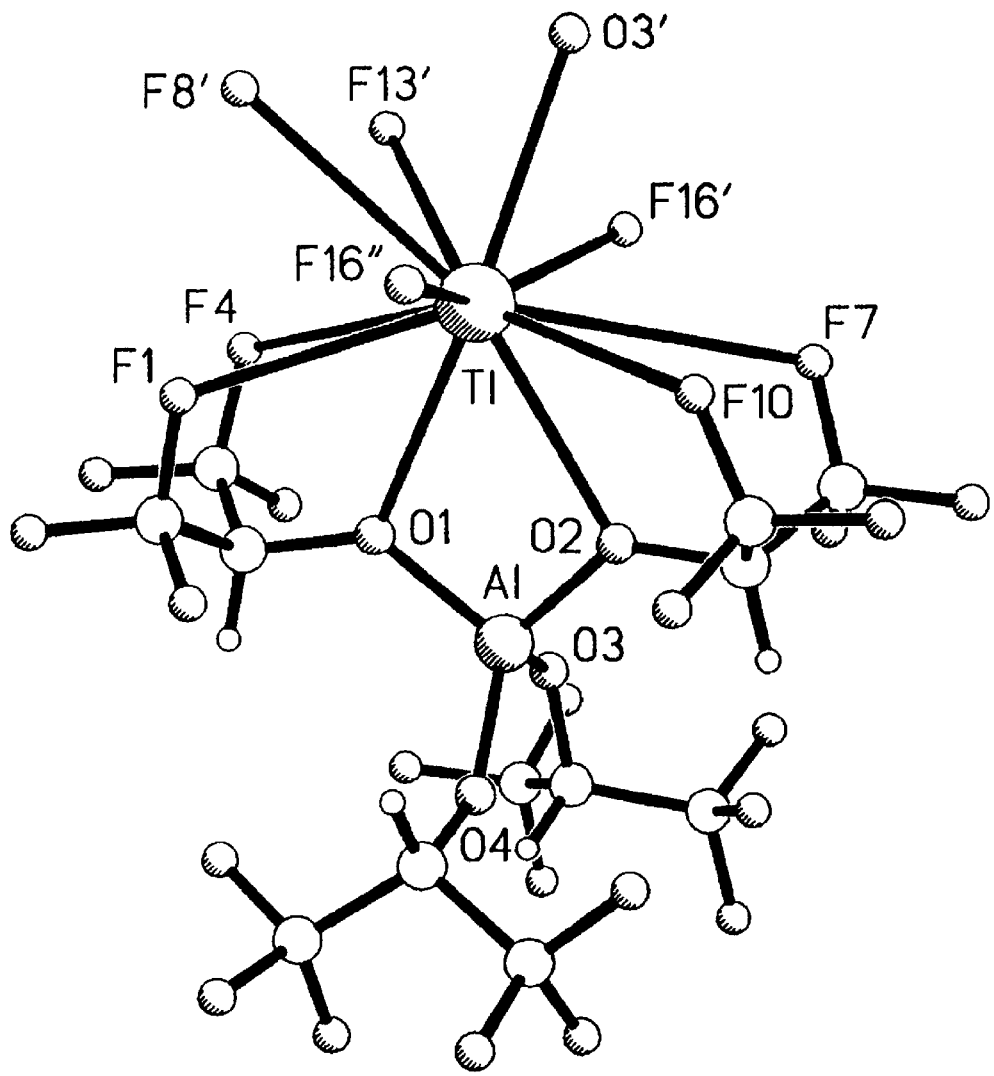
Figure 5. Drawing of the structure of TlAl(OCH(CF$_3$)$_2$)$_4$. The unlabeled shaded circles are fluorine atoms while the unlabeled open circles are carbon atoms (large) or hydrogen atoms (small). Selected interatomic distances (Å) and angles (deg): Tl–O1, 2.805(6); Tl–O2, 2.855(6); Tl–O3', 2.992(6); Tl–F1, 3.090(7); Tl–F4, 3.398(7); Tl–F7, 3.540(6); Tl–F10, 2.967(6); other Tl–F, 3.045(6) to 3.245(6) Å; O1–Tl—O2, 54.3(2).

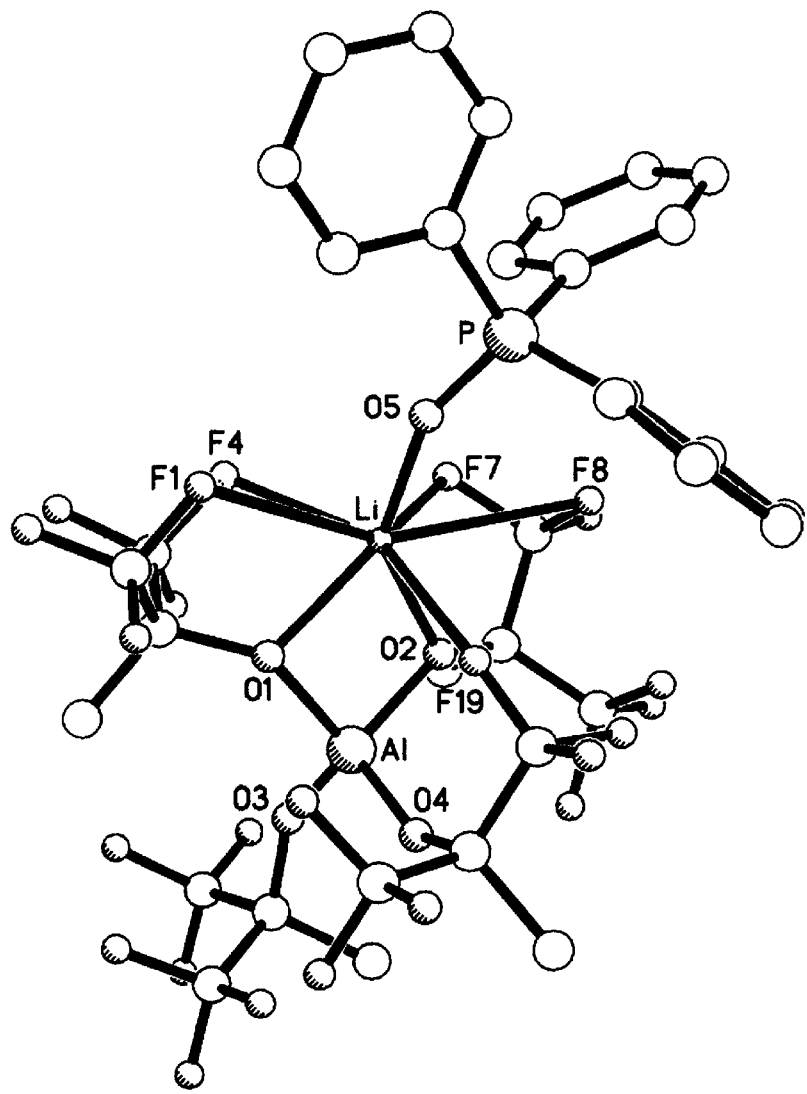
Figure 6. Drawing of the structure of $LiAl(OC(CH_3)(CF_3)_2)_4$ with coordinated triphenylphosphine oxide (hydrogen atoms omitted for clarity). The unlabeled shaded circles are fluorine atoms, while the unlabeled open circles are carbon atoms. Selected interatomic distances (Å) and angles (deg): Li–O1, 2.045(9); Li–O2, 2.018(9); Li–O5, 1.822(9); Li–F1, 2.885(10); Li–F4, 2.308(11); Li–F7, 2.732(11); Li–F8, 2.993(9); Li–F19, 2.827(12); O1–Li–O2, 78.4(3); O1–Al–O2, 92.5(2); Li–O5–P, 155.6(4).

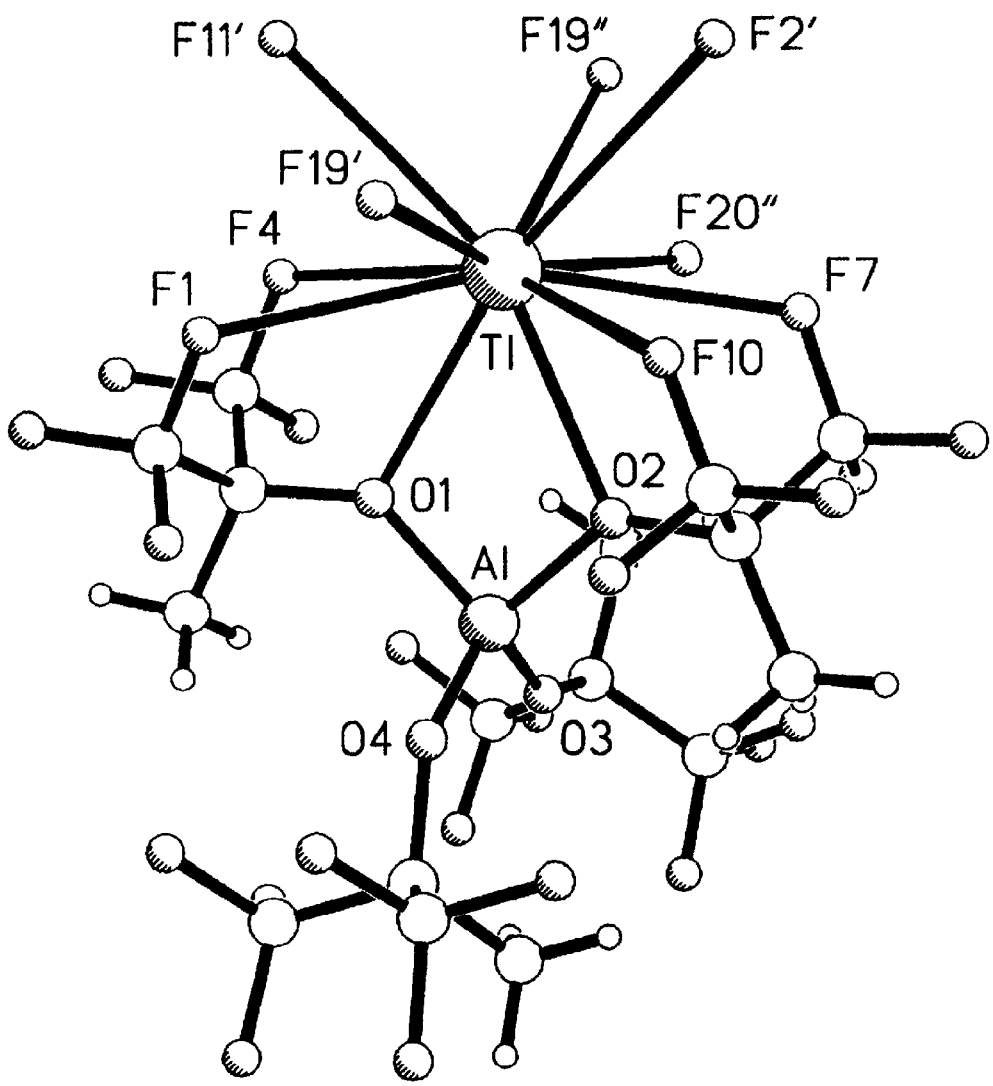
Figure 7. Drawing of the structure of TlAl(OC(CH$_3$)(CF$_3$)$_2$)$_4$. The unlabeled shaded circles are fluorine atoms while the unlabeled open circles are carbon atoms (large) or hydrogen atoms (small). Selected interatomic distances (Å) and angles (deg): Tl–O1, 2.731(9); Tl–O2, 2.717(9); Tl–F1, 3.087(10); Tl–F4, 2.903(9); Tl–F7, 2.952(10); Tl–F10, 3.081(11); other Tl–F, 3.154(10) to 3.471(10) Å; O1–Tl–O2, 57.9(3).

US 6,221,941 B1

WEAKLY COORDINATING ANIONS CONTAINING POLYFLUOROALKOXIDE LIGANDS

CROSS-REFERENCE TO RELATED APPLICATIONS

This application claims the benefit of U.S. Provisional Application No. 60/058,524, filed Sep. 11, 1997.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. CHE-9628769 awarded by National Science Foundation.

FIELD OF THE INVENTION

The present invention relates to a compound containing polyfluoroalkoxides and the use thereof, in particular, for use in batteries.

BACKGROUND OF THE INVENTION

A compound containing a weakly coordinating anion (i.e., an anion that coordinates only weakly with a cation) is useful in a variety of applications including as an electrolyte and a counter-ion for a catalyst in a variety of organic reactions. Some of the useful catalysts containing a weakly coordinating anion are described by Barbarich, et al. in "LiAl(OC(Ph)(CF$_3$)$_2$)$_4$: A Hydrocarbon-Soluble Catalyst For Carbon—Carbon Bond-Forming Reactions", *Organometallics*, 1996, 15, 3776, which is incorporated herein in its entirety.

Investigations of very reactive metal and nonmetal cations continues to spur the development of new weakly coordinating anions. See, for example, Bochmann, *Angew. Chem., Int. Ed. Engl.* 1992, 31 1181; Strauss, *Chem. Rev.* 1993, 93, 927, Strauss, *Chemtracts-Inorganic Chem.* 1994, 6,1; and Seppelt, *Angew. Chem., Int. Ed. Engl.* 1993, 32, 1025. One of the most important uses of weakly coordinating anions is to enhance the catalytic activity of metal cations. Two examples that have received considerable attention recently are metallocene-catalyzed olefin polymerization, and lithium-catalyzed Diels-Alder reactions and 1,4-conjugate addition reactions. See Turner, European Patent Appl. No. 277,004, 1988; Pellecchia et al., *Makromol. Chem., Rapid Commun.* 1992, 13, 265; DuBay et al., *J. Org. Chem.* 1994, 59, 6898; Saidi et al., *Chem. Ber.* 1994, 127, 1761; Kobayashi et al., *Chem. Lett.* 1995, 307; and Arai et al., *Angew. Chem., Int. Ed. Engl.* 1996, 15, 3776.

Useful anions must not only be weakly coordinating, they must also be stable with respect to oxidation and/or fragmentation in the presence of highly electrophilic cations. In addition, an ideal weakly coordinating anion should have a single negative charge dispersed over a large surface composed of relatively nonpolar bonds to weakly basic atoms such as hydrogen or the halogens. Weakly coordinating anions which conform to many, but not all, of these criteria include B(Ar$_f$)$_4^-$ (A$_f$=C$_6$F$_5$ or 3,5-C$_6$H$_3$(CF$_3$)$_2$), CB$_{11}$H$_{12-n}$X$_n^-$ (X=H or I), CB$_9$H$_{10-n}$X$_n^-$ (X=H, Cl, Br or M(OTeF$_5$)$_n^-$ (n=4, M=B; n=6, M=Nb, Sb)).

All of the anions mentioned above have limitations. Some are too strongly coordinating for specific applications. Some are unstable under the harsh chemical conditions where they would be employed. For example, the fluorinated derivatives of BPh$_4^-$ can react with strongly electrophilic cations, causing (i) cleavage of a C—F bond and formation of a bond between the fluorine atom and the cation or (ii) transfer of a fluoroaryl group to the cation. In either case, the cation is no longer reactive or catalytically active.

Other weakly coordinating anions, such as ClO$_4^-$, BF$_4^-$, PF$_6^-$, SbF$_6^-$, B(OTeF$_5$)$_4^-$, and Nb(OTeF$_5$)$_6^-$, are not thermally and/or hydrolytically stable. In addition, lithium salts of such anions, including LiCF$_3$SO$_3$ and LiPF$_6$, have low electrical conductivity in organic solvents, especially organic solvents that are stable in the presence of strong reducing agents such as metallic lithium and related lithium-containing battery anode solutions. Moreover, some lithium salts, such as LiPF$_6$, are known to be unstable and decompose over time.

Still other anions containing boron atoms, and anions containing a carbon atom and a cluster of boron atoms, such as carboranes (e.g., CB$_6$, CB$_9$, CB$_{11}$), are not particularly weakly coordinating because the salts formed therefrom contain at most only one fluorine atom which is bonded to a boron atom.

Recently, polyfluorinated carborane anions that are weakly coordinating and are thermally and/or hydrolytically stable have been disclosed in U.S. patent application Ser. No. 09/049,420, filed Mar. 27, 1998.

Despite the recent advances in weakly coordinating anions, there still is a need for a new weakly coordinating anion. There is also a need for a weakly coordinating anion having a high electrical conductivity in an organic solvent.

SUMMARY OF THE INVENTION

The present invention is directed to a class of novel weakly coordinating anions containing at least one ligand having at least one fluorine atom.

More specifically, the present invention provides an anion of the formula [M$_1$(XC(CF$_a$(R$_1$)$_b$)(CF$_c$(R$_2$)$_d$)R$_3$)$_m$(R$_4$)$_n$]$^{-p}$, and the use thereof, where M$_1$ is a transition metal, or a Group III, IV or V element;

p is 1 or 2;

each X is independently O, S, or NR$_5$R$_6$;

each of R$_1$ and R$_2$ are independently H, halide or C$_1$–C$_4$ alkyl;

each R$_3$ is independently H, C$_1$–C$_4$ alkyl, or C$_4$–C$_{20}$ aryl;

each R$_4$ is independently C$_1$–C$_{10}$ alkyl, C$_1$–C$_{10}$ alkoxide or C$_4$–C$_{20}$ aryloxide;

each of R$_5$ and R$_6$ are independently H or C$_1$–C$_{10}$ alkyl;

each of a and c are independently an integer from 0 to 3;

a+b=3;

c+d=3;

m is an integer from 2 to 8; and n is an integer from 0 to 4;

provided at least one of a or c is not 0. In a preferred compound of the present invention, p is 1, each R$_4$ is independently C$_1$–C$_{10}$ alkoxide or C$_4$–C$_{20}$ aryloxide and when M$_1$ is Al and a and c are 3, R$_3$ is not phenyl or p-methylphenyl.

The present invention also provides an electrolyte for an electrochemical device, comprising the anion of the above described formula having a counter cation M where M is a metal cation, a phosphonium cation, an ammonium cation or a sulfonium cation.

BRIEF DESCRIPTION OF THE DRAWINGS

FIG. 1 is an X-ray crystal structure of one of the two Nb(HFIP)$_6^-$ anions in the asymmetric unit of crystals of [2,6-(CH$_3$)$_2$C$_5$H$_4$N] [Nb(HFIP)$_6$].

FIG. 2 is an X-ray crystal structure of LiAl(HFPP)$_4$.

FIG. 3 is a conductivity data fitted to the empirical VTF equation by non-linear least-squares techniques.

FIG. 4 is an X-ray crystal structure of LiAl(HFPP)$_4$·O (C$_6$H$_8$).

FIG. 5 is an X-ray crystal structure of TlAl(HFIP)$_4$.

FIG. 6 is an X-ray crystal structure of LiAl (HFTB)$_4$·OPPh$_3$.

FIG. 7 is an X-ray crystal structure of TlAl(HFTB)$_4$.

DETAILED DESCRIPTION OF THE INVENTION

The present invention provides a compound comprising an anion of the formula [M$_1$(XC(CF$_a$(R$_1$)$_b$)(CF$_c$(R$_2$)$_d$)R$_3$)$_m$(R$_4$)$_n$]$^{-p}$, and the use thereof, where M$_1$ is a transition metal, or a Group III, IV or V element;

p is 1 or 2;

each X is independently O, S, or NR$_5$R$_6$;

each of R$_1$ and R$_2$ are independently H, halide or C$_1$–C$_4$ alkyl;

each R$_3$ is independently H, C$_1$–C$_4$ alkyl, or C$_4$–C$_{20}$ aryl;

each R$_4$ is independently C$_1$–C$_{10}$ alkyl, C$_1$–C$_{10}$ alkoxide or C$_4$–C$_{20}$ aryloxide;

each of R$_5$ and R$_6$ are independently H or C$_1$–C$_{10}$ alkyl;

each of a and c are independently an integer from 0 to 3;

a+b=3;

c+d=3;

m is an integer from 2 to 8; and n is an integer from 0 to 4;

provided at least one of a or c is not 0. In a preferred compound of the present invention, p is 1, each R$_4$ is independently C$_1$–C$_{10}$ alkoxide or C$_4$–C$_{20}$ aryloxide and when M$_1$ is Al and a and c are 3, R$_3$ is not phenyl or p-methylphenyl. More preferably, the compound of the present invention has a polyfluorinated anion having at least two polyfluorinated alkoxide groups. Hereinafter, a "polyfluorinated anion" refers to an anion of the above described formula.

The polyfluorinated anions of the present invention themselves do not necessarily comprise chemical compounds. Indeed, in an isolable compound, anions must be paired with cations to maintain electroneutrality. Thus, a compound of the present invention is, more accurately, of the formula M$_p$[M$_1$(XC(CF$_a$(R$_1$)$_b$)(CF$_c$(R$_2$)$_d$)R$_3$)$_m$(R$_4$)$_n$]$_k$.

M is a cation having a valence of from 1 to 4. M can be any cation including a cation derived from an alkaline metal; alkaline-earth metal; transition metal such as Ag, Zn, Cu, Co, Fe, Mn, Cr, V, Ti, Zr, Rh, Pd, Cd, Hg, Os, Pt, Y, Nb, Sc, Ta, Hf, and Mo; lanthanide and actinide series metal; ammonium moieties such as ammonium, tetrahydrocarbyl ammonium, e.g., tetrabutyl ammonium and tetraethyl ammonium, trihydrocarbyl ammonium, e.g., triethyl ammonium, diisopropyl ethyl ammonium and trimethyl ammonium, dihydrocarbyl ammonium, nitrogen heteroaromatic cation such as 2,6-lutidinium, methyl 2,6-lutidinium, methyl pyridinium and pyridinium, and imminium cation; phosphonium moieties including tetraalkylphosphonium, tetraaryl phosphonium and phosphonium ions containing a mixture of alkyl and aryl groups; sulfonium moieties such as sulfonium ions containing alkyl, aryl or mixtures thereof; and other suitable cations such as thallium. Furthermore, M can be a relatively stable carbocation such as a trityl moiety and related carbocations (e.g., R$_3$C$^+$); and other known cations such as hydronium (H$_3$O$^+$), H$_5$O$_2^+$, (Et$_2$O)$_n$H$^-$, H$_9$O$_4^+$, and formylium (HCO$^+$). Preferably, the cation (i.e., M) is selected from the group consisting of thallium, alkaline metal cations, ammonium, monohydrocarbyl ammonium, dihydrocarbyl ammonium, trihydrocarbyl ammonium, tetrahydrocarbyl ammonium, nitrogen heteroaromatic cation, tetrahydrocarbyl phosphonium, hydronium, formylium, and trityl and related carbocations; more preferably from the group consisting of trityl and related carbocations, thallium, tetrahydrocarbyl ammonium, alkaline metal cations, and nitrogen heteroaromatic cation; and most preferably from the group consisting of trityl, Li$^+$, Tl$^+$, 2,6-lutidinium, tetraethyl ammonium, sodium, potassium, and methyl 2,6-lutidinium. As used in this invention, a "hydrocarbyl" refers to a compound having at least one carbon atom. Such compounds include aryl, alkyl, alkenyl and alkynyl. Moreover, hydrocarbyl can be straight chain, branched, or cyclic. Hydrocarbyl can also be substituted with other non hydrogen or carbon atoms such as halide, oxygen, sulfur, nitrogen or phosphorus.

It will be appreciated that a molar ratio of a cation to a polyfluorinated anion of the present invention depends on the valence of the cation. This is reflected in the values p and k, for example, if both the cation and the anion are monovalent, then k and p are 1, and there will be a 1:1 molar ratio between the cation and the polyfluorinated anion of the present invention. Whereas if the cation is divalent and the anion is monovalent, then k is 2 and p is 1, and there will be a 1:2 molar ratio between the cation and the polyfluorinated anion of the present invention. Preferably, k is an integer from 1 to 4, more preferably 1 to 3, still more preferably k is 1 or 2, and most preferably 1. Preferably p is 1 or 2 and more preferably 1.

It should be appreciated that because the polyfluorinated anions of the present invention are weakly associating anions, a cation associated with a polyfluorinated anion can be readily exchanged with another cation by any of the known methods including ion exchange chromatography and other ion exchange methods.

As used in this invention, Group III, IV and V elements are those elements which are listed in the Group III, IV and V of the periodic table, respectively. For example, Group III elements are B, Al, Ga, In and Tl; Group IV elements are C, Si, Ge, Sn, and Pb; and Group V elements are N, P, As, Sb and Bi. Preferably M$_1$ is selected from the group consisting of Al, B, V, Ti, Si, Zr, Ge, Sn, Cu, Y, Zn, Ga, Nb, Ta, Bi, P, As, Sc, Hf and Sb, more preferably from the group consisting of Al, B, Nb and Ta, and most preferably from the group consisting of Al, B and Nb.

With reference to the formula described herein:

Preferably, X is O.

Preferably R$_3$ is selected from the group consisting of H, methyl, trifluoromethyl, p-tert-butylphenyl, phenyl, p-methylphenyl and o-(hydroxide)phenyl. As used in this invention, o-(hydroxide)phenyl refers to a phenyl group having an oxygen moiety in ortho-position which is also bound to the M$_1$. For the compound of the present invention, preferably R$_3$ is selected from the group consisting of H, methyl, trifluoromethyl, p-tert-butylphenyl, and phenyl.

Preferably m is 2, 3, 4 or 6. For the compound of the present invention, preferably m is 2, 4 or 6.

Preferably n is 0 or 1.

Preferably R$_4$ is C$_1$–C$_{10}$ alkyl or C$_4$–C$_{20}$ aryloxide. When R$_4$ is a C$_1$–C$_{10}$ alkyl group, preferably the alkyl group is selected from the group consisting of methyl and ethyl. When R$_4$ is a C$_4$–C$_{20}$ aryloxide group, preferably $R_4$ is substituted or unsubstituted (dihydroxide)phenyl, and more preferably o-(dihydroxide)phenyl. As used in this invention, dihydroxide phenyl refers to a catechol derived group in which both of the hydroxide groups are bonded to $M_1$. "Substituted or unsubstituted" refers to the presence or absence of one or more substituents on the phenyl (or other appropriate) ring moiety, respectively. Such substituent can be a halogen; an alkyl group including cyclic alkyl and halogenated alkyl groups; and an aryl group including halogenated aryl and heteroaryl groups.

Alkyl groups according to the present invention are aliphatic hydrocarbons which can be straight or branched chain groups. Alkyl groups optionally can be substituted with one or more substituents, such as a halogen, alkenyl, alkynyl, aryl, hydroxy, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, and pentafluoroethyl. Aryl groups are carbocyclic or heterocyclic aromatic ring moieties. Aryl groups can be substituted with one or more substituents, such as a halogen, alkenyl, alkyl, alkynyl, hydroxy, alkoxy or cycloalkyl. Exemplary aryl groups include, phenyl, p-methylphenyl, p-tert-butylphenyl, thienyl, furanyl, pyrimidinyl, pyridyl, oxazolyl, isoxazolyl, and thiophenyl.

In another embodiment, each of a and c are independently integers from 0 to 3, wherein at least one of a or c is an integer from 1 to 3. Preferably, at least one of a or c is 3. Thus, $M_1$ of the polyfluorinated anion of the present invention may contain a mixture of poly fluorinated alkoxide and non-fluorinated alkoxide ligands. More preferably, a and c are 3.

The polyfluorinated anion of the present invention can also include one or more chelating polyalkoxides such as di- and/or tri-alkoxides. Additionally, the polyfluorinated anion of the present invention can also include one or more alkyl or aryl groups in place of one or more alkoxide groups described above.

A method for preparing the polyfluorinated anion of the present invention will now be described in reference to a synthesis of a compound containing $Nb(HFIP)_6^-$ anion. The method involves relatively inexpensive commercially available compounds: lithium, $NbCl_5$, and hexafluoro-2-propanol. The general reaction scheme for the preparation of compounds containing $Nb(HFIP)_6^-$ is shown below:

$$2\ Li(s) + 2\ HOCH(CF_3)_2 \rightarrow 2\ LiOCH(CF_3)_2 + H_2(g)$$

$$6\ LiOCH(CF_3)_2 + NbCl_5 \rightarrow LiNb(OCH(CF_3)_2)_6 + 5\ LiCl(s)$$

Other counter-cation species, including other metal cations such as K, Na, Mg, Ca, and Cs; trityl cation; pyridinium cations such as 2,6-pyridinium cation; and 2,6-lutidinium cation, can be prepared by cation-exchange reaction, for example, the trityl ($CPh_3^+$) salt can be prepared by metathesis of $LiNb(HFIP)_6$ with $CPh_3Cl$ in 1,2-dichloroethane.

As shown in FIG. 1, $[2,6-(CH_3)_2C_5H_4N][Nb(HFIP)_6]$, i.e., a 2,6-pyridinium salt of $Nb(HFIP)_6^-$ anion, appears to possess a pseudo-octahedral geometry with a $NbO_6$ core, similar to the pseudo-octahedral $ZrO_6$ core of the structurally-characterized $Zr(HFIP)_6^{2-}$ anion in $Tl_2Zr(HFIP)_6$. Without being bound by any theory, it is believed that the $Li^+$ ion in $LiNb(HFIP)_6$ is probably bonded to several alkoxide oxygen atoms and is possibly bonded to several $CF_3$-group fluorine atoms, similar to $Tl^+$ ions in $Tl_2Zr(HFIP)_6$. As shown in FIG. 2, the solid-state structure of the related compound $LiAl(HFPP)_4$ (HFPP=hexafluoro-2-phenyl-2-propoxide) appears to show that the $Li^+$ ion is bonded to two alkoxide oxygen atoms and four $CF_3$-group fluorine atoms from a given $Al(HFPP)_4^-$ anion. For comparison, the $Li^+$ ion in the unfluorinated salt $LiNb(OEt)_6$ is believed to be bonded to only four ethoxide oxygen atoms from two adjacent $Nb(OEt)_6^-$ anions forming a pseudo-tetrahedral $LiO_4$ core.

Compounds containing the polyfluorinated anion of the present invention have high electrical conductivity making them particularly useful as electrolytes for electrochemical devices. Exemplary electrochemical devices include batteries, such as lithium batteries or lithium ion batteries for a variety of applications; other type of batteries; fuel cells; electrical double layer capacitors; sensors; and electrochromic displays. Such electrochemical devices can be used in a variety of applications including electrochemical devices for electric vehicles, lap top computers, and other applications requiring an energy source. As table 1 shows, lithium salts of the polyfluorinated anions of the present invention have high electrical conductivities in organic solvents. Specifically, the compounds of the present invention have high electrical conductivity in tetrahydrofuran (THF) and glyme compare to other fluorine-containing lithium salts such as $LiCF_3SO_3$.

TABLE 1

Electrical Conductivity[1]

| Compound | Conc. (M) | Solvent | Conductivity ($\mu S\ cm^{-1}$) | Eq. Conductivity ($S\ cm^2\ mol^{-1}$) |
|---|---|---|---|---|
| Li (HFIP) | 0.0100 | THF | 0.315 | 0.0315 |
| Li (HFIP) | 0.0100 | glyme | 0 | |
| LiOTf | 0.0100 | THF | 1.47 | 0.147 |
| LiOTf | 0.0100 | glyme | 3.90 | 0.390 |
| LiOTf/1.36 eq. crown | 0.0100 | glyme | 7.00 | 0.700 |
| LiOTf/>50 eq. crown | 0.0100 | glyme | 31.0 | 3.10 |
| LiOTf | 0.0100 | PC | 195 | 19.5 |
| LiAl $(HFPP)_4$ | 0.0100 | THF | 258 | 25.8 |
| LiAl $(HFPP)_4$ | 0.0100 | DFB | 2.72 | 0.272 |
| LiAl $(HFPP)_4$ | 0.0100 | glyme | 250 | 25.0 |
| LiAl $(HFPP)_4$ | 0.0100 | PC | 130 | 13.0 |
| LiAl (t-BuHFPP) | 0.0100 | glyme | 238 | 23.8 |
| LiNb $(HFIP)_6$ | 0.0100 | THF | 337 | 33.7 |
| LiNb $(HFIP)_6$ | 0.0100 | glyme | 360 | 36.0 |
| LiNb $(HFIP)_6$/1.34 eq. crown | 0.0100 | glyme | 338 | 33.8 |
| LiNb $(HFIP)_6$ | 0.0100 | PC | 126 | 12.6 |

[1]HFIP = $OCH(CF_3)_2$; HFPP = $OC(Ph)(CF_3)_2$; crown = 12-crown-4; t-BuHFPP = $OC(p-C(CH_3)_3Ph)((CF_3)_2)$; THF = tetrahydrofuran; PC = propylene carbonate; OTf = $CF_3SO_3$; DFB = 1,2-difluorobenzene Particularly useful lithium salts of the compounds of the present invention in batteries include $LiAl(OC(C_6H_5)(CF_3)_2)_4$, $LiNb(OCH(CF_3)_2)_6$, and LiAl(t-BuHFPP).

Again referring to Table 1, the lithium salts of the polyfluorinated anions of the present invention are at least about two orders of magnitude higher in electrical conductivity than lithium triflate in THF and glyme. Thus, the amount of a compound of the present invention required in an electrochemical device to achieve a similar electrical conductivity in an organic solvent such as THF or glyme is about 1% of the amount of other fluorine-containing electrolytes such as $LiCF_3SO_3$ and $LiPF_6$.

A lithium salt of the polyfluorinated anion of the present invention has an electrical conductivity of at least about 50 $\mu S cm^{-1}$ in THF at about 0.01 M concentration at about 25° C., preferably at least about 130 $\mu S cm^{-1}$, more preferably at least about 190 $\mu S cm^{-1}$, and most preferably at least about 250 μScm$^{-1}$. Alternatively, a lithium salt of the polyfluorinated anion of the present invention has electrical conductivity of at least about 50 μScm$^{-1}$ in glyme at about 0.01 M concentration at about 25° C., preferably at least about 130 μScm$^{-1}$, more preferably at least about 190 μScm$^{-1}$, and most preferably at least about 250 μScm$^{-1}$.

It is believed that the structure of LiAl(HFPP)$_4$ contains a rare trigonal-prismatic coordination sphere around the Li$^+$ cation, with two Li—O(C,Al) bonds and four Li—F(C) bonds, see FIG. 2. Without being bound by any theory, it is believed that the weak bonds between the Li$^+$ cation and the CF$_3$ groups are responsible for the high electrical conductivity in low dielectric solvents. Indeed, it is believed that the high degree or fluorination and the weak coordination between the Li$^+$ cations in the C—F bonds differentiate the lithium salts of the present invention from other fluorine-containing lithium salts, for example, LiNb(HFIP)$_6$ contains an unprecedented 36 fluorine atoms which is believed to delocalize a single negative charge.

The polyfluorinated anions of the present invention can also be used in a variety of organic reaction catalysts where a weakly coordinating anion improves the yield, selectivity and/or the rate of catalytic reaction by the corresponding cation including in catalysts for conjugate additions and Diels-Alder reactions. The compounds of the present invention comprise a weakly coordinating anion, i.e., polyfluorinated anion, which enhances the catalytic activity of the associated metal cation. Exemplary catalytic reactions that have recently received a considerable attention are lithium-catalyzed Diels-Alder reactions and lithium-catalyzed 1,4-conjugate addition reactions. As shown below, using LiNb(HFIP)$_6$, 1, as a catalyst in 1,4-conjugate addition reaction of silyl ketene acetal 2 to the sterically encumbered α,β-unsaturated carbonyl compound 3 gave the 1,4-addition product 4 in 93% yield.

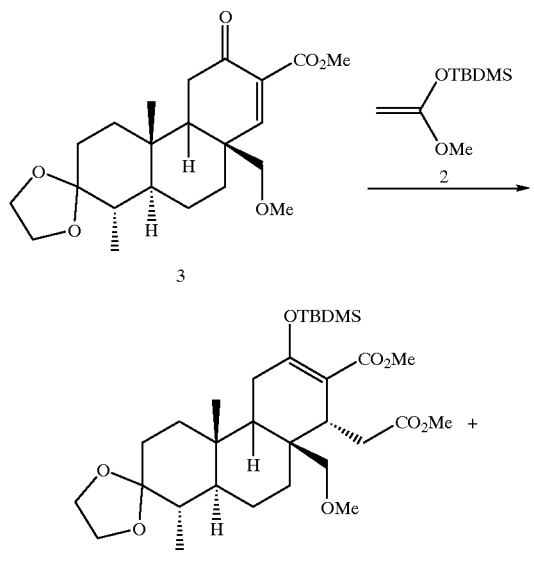

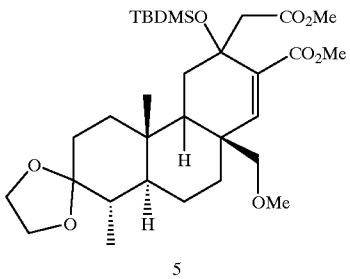

Reaction conditions: 1,2-dichloroethane (DCE) solvent, 0.1 M of 3, 0.2 M of 2, 0.01 M of LiNb(HFIP)$_6$ and 0.01 M of hexamethylphosphoramide (HMPA) at 24° C. for 30 hours. Formation of only the 1,4-addition product 4 was observed under these conditions. Interestingly, when HMPA was left out of the reaction mixture, a mixture of 4 and the 1,2-addition product 5 was observed after only 10 minutes (95% isolated yield, 4:5 mole ratio=1:5). Without being bound by any theory, it is believed that Li$^+$ ion coordinates with HMPA to produce a sterically more hindered enone-lithium ion complex, thus favoring addition of the ketene at a site more distant from the carbonyl carbon, i.e., 1,4-addition, over addition of the ketene to the carbonyl carbon, i.e., 1,2-addition reaction.

A comparison of the ability of LiNb(HFIP)$_6$ and two other lithium catalysts to increase the formation of 1,4-conjugate addition product is shown in Table 2. The weaker Lewis acidity of the Li(HMPA)$^+$ complex results in a decreased reaction rate, which is evidenced by the longer reaction time required when HMPA is added to the reaction mixture. The results obtained with LiNb(HFIP)$_6$ are comparable to the results obtained with the very active catalyst LiCo(C$_2$B$_9$H$_{11}$)$_2$. Product yields were substantially lower when LiClO$_4$ was the catalyst. Furthermore, when LiClO$_4$ was employed in the presence of co-catalyst HMPA, the ratio of 4:5 improved only to 1.3:1. Without being bound by any theory, it is believed that the larger size and/or more weakly coordinating ability of Nb(HFIP)$_6^-$ to Li$^+$ compared with ClO$_4^-$ is responsible for the difference in catalytic activity between LiClO$_4$ and LiNb(HFIP)$_6$.

TABLE 2

Yields of 1,4- and 1,2-addition products 4 and 5, respectively, from lithium-catalyzed reactions between 2 and 3[a]

| catalyst | co-catalyst[b] | time | 4:5 ratio | % yield |
|---|---|---|---|---|
| LiNb(HFIP)$_6$ | none | 10 min | 1:5 | 95% |
| LiNb(HFIP)$_6$ | 0.1 M HMPA | 30 h | 100:0 | 93% |
| LiCo(C$_2$B$_9$H$_{11}$)$_2$[c] | none | 20 min | 1:6 | 95% |
| LiCo(C$_2$B$_9$H$_{11}$)$_2$[c] | 0.1 M HMPA | 32 h | 100:0 | 96% |
| LiClO$_4$ | none | 10 min | 1:4.5 | 62% |
| LiClO$_4$ | 0.1 M HMPA | 48 h | 1.3:1 | 69% |

[a]Reaction conditions: 1,2-dichloroethane, 0.1 M of 3, 0.2 M of 2, 0.1 M of catalyst and 0.1 M of co-catalyst, when appropriate, at 25° C.).
[b]HMPA = hexamethylphosphoramide.
[c]These results are from DuBay et al., J. Org. Chem., 1994, 59, 6898.

The polyfluorinated anions of the present invention that are sterically bulkier, i.e., larger, than Nb(HFIP)$_6^-$ afford lithium-ion catalysts that are more regioselective and/or more active in the absence of HMPA. Moreover, enantiomerically enriched polyfluorinated anions of the present invention containing a polyfluorinated alkoxide having a chiral center afford lithium-ion catalysts that are enantioselective, i.e., produce an enantiomerically enriched product. A chiral center of a carbon atom, of course, is a carbon atom to which four different groups are attached; however, the ultimate criterion of chirality of a compound is nonsuperimposability on the mirror image. Facially selective, enantioselective or stereoselective synthetic reactions are those in which one of a set of stereoisomers is formed predominantly or exclusively. Preferably, one isomer is produced in at least about 50 percent enantiomeric excess. Enantiomeric excess is the amount of difference between one enantiomer and the other enantiomer in the product composition. Enantiomeric excess can be expressed by the following formula: % ee=(R−S)/(R+S), where R is amount of one enantiomer and S is the amount of the other enantiomer, for example, % ee of a product composition containing 98% of one enantiomer and 2% of the other enantiomer is 96%. More preferably, one isomer is produced in at least about 80 percent enantiomeric excess, still more preferably at least about 90 percent enantiomeric excess, even more preferably at least about 95 percent enantiomeric excess, and most preferably at least about 98 percent excess over the other enantiomer.

The lithium salts of the polyfluorinated anions of the present invention can be combined or mixed with a polymer to prepare polymeric materials that exhibit lithium ion conductivity. Such materials, referred to as salt-in-polymer solid electrolytes or solid polymer electrolytes, can be used as electrolytes for solvent-free high-energy-density lithium-based batteries. A polymer can also include a linker which allows a direct linkage of the compound of the present invention to the polymeric structure by a chemical bond formation between the polymer and the compound of the present invention. The polymers useful for the present invention have a rubbery physical characteristic. Generally, suitable polymers have one or more of the following identifying characteristics: 1) ability to dissolve lithium salts of weakly coordinating anions and/or to coordinate, albeit weakly, to the lithium cations of lithium salts of weakly coordinating anions; 2) ability to maintain low glass-transition temperatures with varying amounts of lithium salts dissolved therein; and 3) the ability to possess high electrical conductivities, especially high lithium-ion conductivities, i.e., higher than lithium triflate/polymer mixture at a given temperature). Exemplary polymers useful for the present invention include polyethylene glycol; polyethylene; polypropylene; polystyrene; polybutadiene; poly (vinyl fluoride); polychloroprene; poly(alkyl siloxane) such as poly(dimethylsiloxane); poly(vinyl chloride); poly (ethylene imine); and poly(alkylene oxide) such as poly (propylene oxide), amorphous poly(ethylene oxide) and poly(ethylene oxide). Preferably the polymer is selected from the group consisting of amorphous polyethylene oxide (aPEO), poly(alkylene oxide), poly(alkyl siloxane), poly (vinyl fluoride), poly(vinyl chloride), polychloroprene, polybutadiene, polyethylene and poly propylene; more preferably from the group consisting of aPEO, poly(vinyl fluoride), poly(vinyl chloride), polychloroprene, polybutadiene, polyethylene and polypropylene; and most preferably from the group consisting of aPEO, polybutadiene, polyethylene and polypropylene.

The present invention also includes salt-in-polymer electrolytes having alkali metal salts containing the polyfluorinated anions of the present invention including polyfluorinated anions such as $Nb(HFIP)_6^-$, $Al(OCH(CF_3)_2)_4^-$, $Al(OC(CH_3)(CF_3)_2)_4^-$, $Al(OCPh(CF_3)_2)_4^-$, and $Al(OC(CF_3)_3)_4^-$. Compounds containing these polyfluorinated anions have superior glass transition temperatures, impedance measurements and cation transference numbers than compounds containing other anions.

The polyfluorinated anions of the present invention can also be used as co-catalysts for activating transition-metal-catalyzed olefin polymerization and as counterions for polymerization photoinitiators.

Additional objects, advantages, and novel features of this invention will become apparent to those skilled in the art upon examination of the following examples thereof, which are not intended to be limiting.

Experimental

All preparations and physical measurements were carried out with rigorous exclusion of air and water. Schlenk, glovebox, and high vacuum techniques were employed, with purified nitrogen used when an inert atmosphere was required. All reagents and solvents were reagent grade or better. Lithium wire (Aldrich, Milwaukee, to Wis.) was used as received. Chlorotriphenylmethane, $CPh_3Cl$(Aldrich), was recrystallized from ethyl acetate. Niobium(V) chloride (Aldrich) was sublimed under vacuum at 125° C. Hexafluoro-2-propanol (Central Glass, Ube, Japan) was dried over activated 4 Å molecular sieves and vacuum distilled. The following solvents were dried by distillation from the indicated drying agent: tetrahydrofuran (Na); benzene-$d_6$ (Na); acetone-$d_6$ (activated 4 Å molecular sieves); acetonitrile-$d_3$ ($P_2O_5$); 1,2-dimethoxyethane (Na); propylene carbonate (Na); hexafluoroisopropanol (activated 4 Å molecular sieves); hexafluoro-2-phenyl-2-propanol (activated 4 Å molecular sieves); diethyl ether (Na); 1,2-dichloroethane ($P_2O_5$); 1,2-dichloroethane-$d_4$ ($P_2O_5$) ; toluene-$d_8$ (Na); acetonitrile-$d_3$ ($P_2O_5$); nitromethane-$d_3$ ($P_2O_5$); chloroform-d ($P_2O_5$); chlorotrifluoromethane ($P_2O_5$); tetramethylsilane ($P_2O_5$); hexamethylphosphoramide ($P_2O_5$); diethyl ether (Na); perfluoro-t-butanol (activated 4 Å molecular sieves); hexafluoro-t-butanol (activated 4 Å molecular sieves); and hexafluorobenzene (activated 4 Å molecular sieves). Purified, anhydrous hexane was prepared by stirring over $H_2SO_4$, flowing through activated basic alumina (Aldrich; 150 mesh), and distilling from sodium metal.

NMR spectroscopy were recorded using a Bruker WP-300 spectrometer or a Bruker SY-200 spectrometer. Chemical shifts ($\delta$) are relative to $SiMe_4$ ($\delta$=0 for $^1H$ NMR) and $CFCl_3$ ($\delta$=0 for $^{19}F$ NMR). ICP-AES analyses were performed using a Perkin Elmer P400 spectrometer as previously described.

Glass transition temperatures ($T_g$) were measured by differential scanning calorimetry using a Perkin Elmer DSC-7 thermal analyzer. The instrument was calibrated by using four standards (gallium, cyclohexane, decane, and heptane). Four different scan rates were used for each sample, and $T_g$ was determined by extrapolating the linear $T_g$ vs. scan rate plots to a scan rate of 0° C./min (the glass transitions were taken as the midpoint of the inflection).

Conductivities of the polymer electrolytes were measured at temperatures between 10° C. and 100° C. and at frequencies between 5 Hz and 5 MHz using a Hewlett-Packard 4192A impedance analyzer. Samples were pressed into pellets within a 0.1 cm Teflon spacer (1.0 cm inside diameter) between two tantalum electrodes. To ensure good contact between the electrodes and the sample, the loaded cells were heated to 80° C. overnight before the dielectric measurements were made. A Nyquist® plot (imaginary vs. real impedance) was used to determine the real (zero frequency) d.c. conductivity of the sample at each temperature.

Negative- and positive-ion electrospray mass spectrometry was performed on a Fisons VG Quattro-SQ mass spectrometer. Conductimetry was performed using a Yellow Springs Instrument Co., Inc. Model 31A conductance bridge and a YSI Model 3403 conductance cell that was calibrated for inverted use (cell constant k=1.113). Solutions for conductance measurements were prepared in a glovebox in 5 mL volumetric flasks with the appropriate dry solvent. The conductance of all solvents was determined to be less than $2 \times 10^{-7}$ $\Omega^{-1}$, the lowest conductance measurable with this apparatus.

Experiment 1

Synthesis of $LiNb(HFIP)_6$

A 25-mL hexafluorobenzene solution of freshly sublimed Li(HFIP) (6.64 g, 38 mmol) was added dropwise to a 25-mL hexafluorobenzene solution of freshly sublimed $NbCl_5$ (1.72 g, 6.4 mmol). The reaction mixture was stirred for 17 hours at 25° C., after which solid LiCl and the small amount of excess $NbCl_5$ was removed by filtration with a fine frit. Volatiles were removed from the colorless filtrate by vacuum evaporation, yielding 5.54 g of $LiNb(HFIP)_6$ as a white solid (79% based on Li(HFIP)).

$^1$H NMR (benzene-$d_6$:hexafluorobenzene (1:9 v:v)): δ 5.19 (m).

$^{19}$F NMR spectrum: δ −74.7 (s)

The molar ratio of niobium to lithium in the product was determined by inductively coupled plasma atomic emission spectrometry (AES-ICP). Calc'd, Nb/Li=1.00. Found (six determinations) Nb/Li=1.03(1).

Experiment 2

Synthesis of $[Ph_3C][Nb(HFIP)_6]$

Freshly prepared $LiNb(HFIP)_6$ (1.64 g, 1.49 mmol) and $Ph_3CCl$ (0.42 g, 1.49 mmol) were dissolved in 35 mL of 1,2-dichloroethane. The yellow solution was protected from light and stirred for 24 hours, after which solid LiCl was removed by filtration with a fine frit. Volatiles were removed from the filtrate by vacuum evaporation, yielding 1.63 g of $[Ph_3C][Nb(HFIP)_6]$ as a yellow solid (82% based on $LiNb(HFIP)_6$).

$^1$H NMR (1,2-dichloroethane-$d_4$): δ 8.29(t), 7.88 (t), 7.66(d) and 5.10 (m).

$^{19}$F NMR: δ −74.6 (s).

Experiment 3

This example illustrates a method for preparing salt-in-polymer electrolytes containing the polyfluorinated anion of the present invention.

Samples of aPEO containing different stoichiometric amounts of $LiNb(HFIP)_6$ were prepared as follows. A sample of the polymer (typically 0.13 g, 3.0 mmol ether-oxygen atoms) was mixed with tetrahydrofuran (7 mL). The resulting mixture was mixed with a tetrahydrofuran solution containing varying amounts of $LiNb(HFIP)_6$ so that the ether-oxygen/lithium molar ratio was 12, 24, or 30. The reaction mixture was stirred for 15 hours, after which time a colorless homogeneous solution was observed. Volatiles were removed from the reaction mixture by vacuum evaporation, resulting in a clear, colorless, rubbery solid on the walls of the flask. The rubbery solid was heated under vacuum at 60° C. for 12 hours to ensure complete removal of tetrahydrofuran. The three clear, colorless, rubbery, salt-in-polymer electrolytes prepared in this way were $aPEO_{12}LiNb(HFIP)_6$, $aPEO_{24}LiNb(HFIP)_6$, and $aPEO_{30}LiNb(HFIP)_6$.

Experiment 4

This example shows the comparison of thermal and conductivity parameters between the solid salt-in-polymer electrolytes of the present invention and other fluoride-containing salt-in-polymer electrolytes.

The glass-transition temperatures, $T_g$, and temperature-dependent conductivities, σ, of the polymeric materials $aPEO_{12}LiNb(HFIP)_6$, $aPEO_{24}LiNb(HFIP)_6$, and $aPEO_{30}LiNb(HFIP)_6$ were determined by differential scanning calorimetry and complex impedance measurements, respectively. The conductivity data, shown in FIG. 3, were fitted to the empirical VTF equation by non-linear least-squares techniques:

$$\sigma = AT^{-1/2} e^{(-B/k(T-T^0))}$$

The preexponential factor, A, is typically dependent on the concentration of charge carriers, B is a pseudo-activation energy believed to be related to the expansivity of the polymer required for ion migration, $T_0$ is related to the glass transition temperature of the polymer electrolyte (typical $T_g-T_0$ values are 25–50° K.), and k is the Boltzmann constant. The parameter $T_0$ was fixed by trial and error to determine the best fit to the data. Values for $T_g$, $T_0$, and the least-squares variables A and B (with their associated estimated standard deviations) are listed in Table 3, along with results for polymer electrolytes composed of aPEO and either $LiCF_3SO_3$ or $NaCF_3SO_3$.

For a given cation, polymer, and stoichiometry, the ionic conductivity of some salt-in-polymer electrolytes can vary as a function of anion. The variations in conductivity may be a function of anion size, polarizability, and/or coordinating ability (i.e., ion-pairing ability), any of which may affect $T_g$, cation-anion clustering, or ion-mediated transient crosslinking of polymer segments or chains.

Transference numbers (i.e., the fraction of charge carried by the cation and the anion), which may not be determined by conductivity measurements alone, may be different for $aPEO_n LiNb(HFIP)_6$ and $aPEO_n LiCF_3SO_3$ at constant n. Pulsed-field-gradient NMR measurements have shown that the transference number of Li$^+$ in $aPEO_n LiCF_3SO_3$ can be less than 0.1 (i.e., the $CF_3SO_3^-$ transference number can be greater than 0.9). The greater volume of the $Nb(HFIP)_6^-$ anion relative to $CF_3SO_3^-$ should lead to a lower anion transference number for $aPEO_n LiNb(HFIP)_6$ than for $aPEO_n LiCF_3SO_3$ at constant n. Therefore, even though the total conductivity of $aPEO_{24}LiNb(HFIP)_6$ and $aPEO_{25}LiCF_3SO_3$ are essentially the same, the lithium-ion conductivity of $aPEO_{24}LiNb(HFIP)_6$ may be substantially higher than that of $aPEO_{25}LiCF_3SO_3$.

TABLE 3

Thermal and conductivity parameters for solid salt-in-polymer electrolytes[a]

| polymer electrolyte | $T_g^b$ (° K.) | $10^6$ $S^{c}$ (S cm$^{-1}$) | $A^d$ (S cm$^{-1}$ K$^{1/2}$) | $B^d$ (eV) | $T_0^d$ (K.) | $T_g-T_0$ (K.) |
|---|---|---|---|---|---|---|
| aPEO[e] | 211 | | | | | |
| $aPEO_{30}LiNb(HFIP)_6$ | 219 | 5.0 | 0.40 (2) | 0.0745 (6) | 190 | 29 |
| $aPEO_{24}LiNb(HFIP)_6$ | 222 | 10 | 0.160 (4) | 0.0545 (3) | 200 | 22 |
| $aPEO_{12}LiNb(HFIP)_6$ | 227 | 1.4 | 2.4 (2) | 0.130 (2) | 180 | 47 |
| $aPEO_{30}LiCF_3SO_3$[f] | | 28 | | | | |
| $aPEO_{25}LiCF_3SO_3$[f] | | 33 | | | | |
| $aPEO_{10}LiCF_3SO_3$[f] | | 3.6 | | | | |
| $aPEO_9LiCF_3SO_3$[e] | 252 | 0.82 | | | | |
| $aPEO_9NaCF_3SO_3$[g] | 251 | 1.5 | 93 | 0.13 | 194 | 57 |
| $aPEO_{12}NaCF_3SO_3$[h] | 236 | 2.6 | 4.0 | 0.080 | 211 | 25 |

[a]aPEO = amorphous polyethylene oxide.
[b]glass-transition temperature.

TABLE 3-continued

Thermal and conductivity parameters for solid salt-in-polymer electrolytes[a]

| polymer electrolyte | $T_g$[b] (°K.) | $S^c$ [(S cm$^{-1}$ K$^{1/2}$)] $10^6$ $S^c$ (S cm$^{-1}$) | $A^d$ (S cm$^{-1}$ K$^{1/2}$) | $B^d$ (eV) | $T_0^d$ (K.) | $T_g$-$T_0$ (K.) |
|---|---|---|---|---|---|---|

[c]D.C. conductivity at 20° C.
[d]A and B are least-squares parameters (esds in parentheses) for s vs. 1/T plots fitted to the VTF equation. $T_0$ values were fixed at values determined by successive iterations to obtain the best fits to the data.
[e]Besner et al., Macromolecules, 1992, 25, 6480.
[f]See reference 44 of Rockwell et al., Inorg. Chimica Acta 1997, 263, 195.
[g]Wintergill et al., Polymer, 1989, 30, 1123.
[h]Doan et al., Chem. Mater., 1990, 2, 539.

Experiment 5

Synthesis of LiB[O($C_6H_4$)C($CF_3$)$_2$O]$_2$

To a solution of HO($C_6H_4$)C($CF_3$)$_2$OH (0.2242 g, 0.86 mmol) in 20 mL distilled $H_2O$ was added a solution of LiOH.$H_2O$ (0.0181 g, 0.43 mmol) and B(OH)$_3$ (0.0266 g, 0.43 mmol) in $H_2O$. The reaction mixture was stirred at 105° C. for 22 h under argon atmosphere. Water was removed using a rotary evaporator to leave a clear, colorless oil. Addition of toluene resulted in precipitation of a white solid. Toluene was removed under vacuum and the resulting white powder was sublimed at 180° C. under vacuum to yield LiB[(O($C_6H_4$)C($CF_3$)$_2$O)]2 as a white powder.

$^1$H NMR (CD$_3$CN) δ 7.37 (doublet, 1H), 7.24 (triplet, 1H), 6.79 (triplet, 1H), 6.7 (doublet, 1H).

$^{19}$F NMR (CD$_3$CN) δ singlet 115.78.

Low resolution mass spectrum (Negative ion electrospray, CH$_3$CN solution). Calc'd for $C_{18}H_8BF_{12}O_4$ 527.0]. Found: m/z 527.1 [(M—Li)$^-$.

Experiment 6

Synthesis of LiAl[O($C_6H_4$)C($CF_3$)$_2$O]$_2$

About 0.515 g of HO($C_6H_4$)C($CF_3$)$_2$OH (1.98 mmol) and 0.155 g of LiAlH$_4$ (4.09 mmol) were mixed in toluene and stirred for 140 h. The reaction mixture was filtered through a Schlenk filter with Celite. The filtrate was concentrated under vacuum to leave a brown solid.

$^1$H NMR ($C_6D_6$) δ 7.76 (doublet, 1H), 7.37 (doublet, 1H), 6.93 (triplet, 1H), 6.73 (triplet, 1H), 6.65 (triplet, 1H), 6.56 (triplet, 1H), 6.45 (doublet, 1H), 6.03 (doublet, 1H).

$^{19}$F NMR ($C_6D_6$) δ -72.47 (multiplet), -74.06 (multiplet), -78.15 (multiplet), -78.75 (multiplet).

Experiment 7

Synthesis of LiAl(HFPP)$_4$

A 20 mL hexane solution of H[HFPP] (5.3624 g, 22.0 mmol) was added to a stirred slurry of LiAlH$_4$ (0.4220 g, 11.1 mmol) in hexane (30 mL). Gas evolution, presumably $H_2$, was observed from the colorless slurry. The mixture was stirred for 16 h, during which time the appearance of the mixture did not change. The mixture was then filtered through a medium glass filter. The remaining solid was washed with 20 mL of hexane. The filtrate was concentrated under vacuum to yield a white crystalline solid (5.2445 g, 95 based on H[HFPP]).

$^1$H NMR ($C_6D_6$): δ 7.9 (multiplet, 8H), 7.0 (multiplet, 12H).

$^{19}$F NMR ($C_6D_6$): δ -75.24 (quartet, $J_{F-Li}$=2.8 Hz).

$^7$Li NMR ($C_6D_6$): δ -0.35 (broad singlet). $^{13}$C NMR (methylcyclohexane-d$_{14}$): δ 131.5 (singlet), 130.3 (singlet), 128.6 (singlet), 127.4 (singlet), 124.5 (quartet, $J_{C-F}$=289 Hz).

Low resolution mass spectrum (Negative ion electrospray, CH$_3$CN solution) m/z 998.9 [(M—Li)$^-$; calcd for $C_{36}H_{20}AlF_{24}O_4$ 999.1]

The X-ray structure of LiAl(HFPP)$_4$ is shown in FIG. 2 (hydrogen atoms are omitted for clarity). The unlabeled shaded circles are fluorine atoms, while the unlabeled open circles are carbon atoms. Selected interatomic distances (Å) and angles (deg.): Li-O1, 1.978(8); Li-O2, 1.966(8); Li-F1, 1.984(9); Li-F4, 2.354(10); Li-F7, 2.098(11); Li-F10, 2.082 (9); O1-Li-O2, 79.9(3).

Experiment 8

Synthesis of LiAl(HFPP)$_4$.O(C6H$_8$)

LiAl(HFPP)$_4$ was dissolved in toluene, and slightly less than one equivalent of cyclohexenone was added.

The X-Ray structure of LiAl(HFPP)$_4$ with coordinated 2-cyclohexen-1-one is shown in FIG. 4 (hydrogen atoms are omitted for clarity). The unlabeled shaded circles are fluorine atoms, while the unlabeled open circles are carbon atoms. Selected interatomic distances (Å) and angles (deg.): Li-O1, 2.028(9); Li-O2, 2.02(1); Li-O5, 1.830(9); Li-F1, 2.27(1); Li-F4, 2.48(1); Li-F7, 2.75(1); O5-C32, 1.230(6); O1-Li-O2, 78.1(3); O1-Al-O2, 92.1(2); Li-O5-C32, 154.1 (6).

Experiment 9

Synthesis of [($C_6H_5$)$_3$C][Al(HFPP)$_4$]

Upon addition of a CH$_2$Cl$_2$ solution of LiAl(HFPP)$_4$ (0.2082 g, 2069 mmol) to a CH$_2$Cl$_2$ solution of Ph$_3$CCl (0.0576 g, 0.2066 mol) at −78° C., a bright orange color developed. The solution was warmed to room temperature and stirred for 15 h with the formation of a precipitate. The solution was filtered through a medium glass filter covered with Celite yielding a bright orange solution. The filtrate was concentrated to yield a yellow solid which was then dissolved in hot CHCl$_3$. Upon cooling to −40° C., yellow crystals formed (0.2265 g, 88.2%).

$^1$H NMR (CD$_2$Cl$_2$) δ 8.4 (triplet of triplets, 3H), 7.85 (multiplet, 14H), 7.61 (doublet of multiplets, 6H), 7.27 (triplet of triplets, 4H), 7.16 (triplet of multiplets).

$^{19}$F NMR (CH$_2$Cl$_2$) δ -74.8 (singlet)

Experiment 10

Synthesis of TlAl(HFIP)$_4$

A toluene solution of Tl[HFIP] (3.8849 g, 10.35 mmol) was added dropwise from an addition funnel to a stirred slurry of AlCl$_3$ (0.3455 g, 2.59 mmol) in toluene at 0° C. Upon addition, a white precipitate, presumably TlCl, formed. Following addition, the solution was warmed to room temperature and the clear colorless solution with the white precipitate was stirred for five hours during which time no change was observed. The reaction mixture was concentrated under vacuum overnight to yield white solid which was still moist with, presumably, toluene. Sublimation at 50° under vacuum gave TlAl(HFIP)$_4$ as a white solid(1.6072 g, 68.7%).

$^1$H NMR ($C_6D_6$) δ 4.65 (septet, $J_{H-F}$=6.3 Hz).

$^{19}$F NMR ($C_6D_6$) δ -76.46 (doublet, $J_{H-F}$=6 Hz).

The X-Ray structure of TlAl(HFIP)$_4$ is shown in FIG. 5. The unlabeled shaded circles are fluorine atoms, while the unlabeled large open circles are carbon atoms and unlabeled small open circles are hydrogen atoms. Selected interatomic distances (Å) and angles (deg.): Tl-O1, 2.805(6); Tl-O2, 2.855(6); Tl-O3', 2.992(6); Tl-F1, 3.090(7); Tl-F4, 3.398(7); Tl-F7, 3.540(6); Tl-F10, 2.967(6); other Tl-F, 3.045(6) to 3.245(6) Å; O1-Tl-O2, 54.3(2).

Experiment 11

Synthesis of TlB(HFIP)$_4$

About 0.3524 g of B(HFIP)$_3$ (0.688 mmol) was vacuum transferred to a frozen toluene solution of Tl(HFIP) (0.2564 g, 0.690 mmol). The mixture was stirred at room temperature overnight (approximately 18 h). The reaction mixture was concentrated under vacuum to provide a solid. The solid was sublimed under vacuum at 45° C. to yield TlB(HFIP)$_4$ as a white solid (0.3187 g, 52.4% yield).

$^1$H NMR (CD$_2$Cl$_2$) δ 4.80 (septet).

$^{19}$F NMR (C$_6$D$_6$) δ −73.93 (doublet, J$_{H-F}$=6 Hz).

Experiment 12

Synthesis of LiAl(HFTB)$_4$

A 10 mL hexane solution of H[HFTB] (2.3643 g, 13.0 mmol) was added to a stirred slurry of LiAlH$_4$ (0.246 g, 6.49 mmol) in hexane (40 mL) at room temperature. After about 52.5 h, the reaction mixture was filtered through a medium glass filter to remove white solid. The white solid was washed with 30 mL of hexane. The filtrate was concentrated under vacuum to yield LiAl(HFTB)$_4$ as a white crystalline solid (1.7561 g, 71% based on H[HFTB]).

$^1$H NMR (C$_6$D$_6$) δ 1.43 (singlet).

$^{19}$F NMR (C$_6$D$_6$) δ −79.72 (singlet).

Low resolution mass spectrum (Negative ion electrospray, CH$_3$CN solution). Calc'd for C$_{16}$H$_{12}$AlF$_{24}$O$_4$ 751.0 Found m/z 750.8 [(M—Li)]$^-$.

Experiment 13

Synthesis of LiAl(HFTB)$_4$·OP (C$_6$H$_5$)$_3$

About one equivalent of triphenylphosphine oxide was added to a hexane solution containing LiAl(HFTB)$_4$.

The X-Ray structure of LiAl(HFTB)$_4$ with coordinated triphenylphosphine oxide is shown in FIG. 5 (hydrogen atoms are omitted for clarity). The unlabeled shaded circles are fluorine atoms, while the unlabeled open circles are carbon atoms. Selected interatomic distances (Å) and angles (deg.): Li-O1, 2.045(9); Li-O2, 2.018(9); Li-O5, 1.822(9); Li-F1, 2.885(10); Li-F4, 2.308(11); Li-F7, 2.732(11); Li-F8, 2.993(9); Li-F19, 2.827(12); O1-Li-O2, 78.4(3); O1-Al-O2, 92.5(2); Li-O5-P, 155.6(4).

Experimental 14

Synthesis of TlAl(HFTB)$_4$

A toluene solution of TL[HFTB] (7.8089 g, 20.26 mmol) was added dropwise using an addition funnel to a stirred slurry of AlCl$_3$ (0.6753 g, 5.065 mmol) in toluene at 0° C. Upon addition, a white precipitate, presumably TlCl, formed immediately. Following addition, the solution was warmed to room temperature and the clear colorless solution with the white precipitate was stirred for 16 h during which time no change was observed. The reaction mixture was then concentrated under vacuum overnight to yield a white solid which was still moist with, presumably, toluene. Sublimation of the solid at 60° C. under vacuum (4.1064 g, 84.9%) gave TlAl (HFTB)$_4$.

$^1$H NMR (C$_6$D$_6$) δ 1.57 (singlet).

$^{19}$F NMR (C$_6$D$_6$) δ −77.89 (singlet).

The X-Ray structure of TlAl (HFTB)$_4$ is shown in FIG. 5. The unlabeled shaded circles are fluorine atoms, while the unlabeled large open circles are carbon atoms and small open circles are hydrogen atoms. Selected interatomic distances (Å) and angles (deg.): Tl-O1, 2.731(9); Tl-O2, 2.717 (9); Tl-F1, 3.987(10); Tl-F4, 2.903(9); Tl-F7, 2.952(10); Tl-F10, 3.081(11); other Tl-F 3.154(10) to 3.471(10)Å; O1-Tl-O2, 57.9(3).

Experiment 15

Synthesis of [(C$_6$H$_5$)$_3$C][Al(HFTB)$_4$]

Upon addition of a CH$_2$Cl$_2$ solution of TlAl(HFTB)$_4$ (3.994 g, 3.663 mmol) to a CH$_2$Cl$_2$ solution of Ph$_3$CCl (1.0214 g, 3.664 mmol) at −78° C., a bright orange color developed and a precipitate formed. The solution was warmed to room temperature and stirred for 20 h. The solution was then filtered through a medium glass filter covered with Celite yielding a bright orange solution. The filtrate was concentrated under vacuum yielding a yellow solid (3.2034 g crude, 87.9%). The yellow solid was washed with isooctane. Recrystallization from hot CHCl$_3$ with cooling to −40° C. gave yellow crystals (2.4 g, 66.7%).

$^1$H NMR (CD$_2$Cl$_2$) δ 8.4 (triplet, 3H), 7.85 (triplet, 6H), 7.61 (doublet, 6H), 1.47 (singlet, 12H).

$^{19}$F NMR (CH$_2$Cl$_2$) δ −79.85 (singlet).

Experiment 16

Synthesis of LiAl(t-BuHFPP)$_4$

About 0.9923 g of (t-BuHFPP)H (3.31 mmol) and LiAlH$_4$ (0.1265 g, 3.34 mmol) were added to about 50 mL of hexane. The mixture was stirred at room temperature for 18 h and filtered. The filtrate was concentrated to yield 0.2899 g of LiAl(t-BuHFPP)$_4$. An additional 0.4783 g of LiAl(t-BuHFPP)$_4$ was obtained by washing the filtered solid with toluene. Total yield was 47%. LiAl(t-BuHFPP)$_4$ is a white solid.

$^1$H NMR (C$_6$D$_6$) δ 7.95 (doublet, 2H), 7.23 (doublet, 2H), 1.12 (singlet, 9H).

$^{19}$F NMR (CH$_2$Cl$_2$) δ −75.32 (singlet).

Experiment 17

Synthesis of LiAl(PFTB)$_4$

A 15 mL CFC-113 solution of H[PFTB] (1.5577 g, 6.599 mmol) was added to a stirred slurry of LiAlH$_4$ (0.1250 g, 3.299 mmol) in CFC-113 (30 mL). The reaction mixture was stirred for 16.5 h and filtered through a medium glass filter. The filtrate was concentrated under vacuum to yield a white crystalline solid (1.2302 g, 76.6% based on H[PFTB]).

$^{19}$F NMR (C$_6$D$_6$) δ −61.00 (singlet).

Low resolution mass spectrum (Negative ion electrospray, CH$_3$CN solution). Calcd for C$_{16}$AlF$_{36}$O$_4$ 967.1. Found m/z 966.5 (M—Li)$^-$.

Experiment 18

Synthesis of [2,6dimethylpyridinium][Nb(HFIP)$_6$]

A mixture of freshly prepared LiNb(HFIP)$_6$ (0.20 g, 0.18 mmol) and 2,6-dimethylpyridinium chloride (0.026 g, 0.18 mmol) was dissolved in 25 mL of dry dichloromethane. The reaction was stirred vigorously at room temperature for 2.5 h, at which time solid LiCl was removed by filtration through a fine frit. The volume of the filtrate was reduced under vacuum to approximately 5 mL until the product began to precipitate from solution. The solution was then heated until all the solid had redissolved. This saturated solution was allowed to cool slowly to room temperature. After 18 h, the first of two batches of crystals was collected. This process was repeated and the second batch of crystalline material was collected. Both portions were combined (0.20 g, 93% yield by LiNb(HFIP)$_6$).

A ball and stick representation of the X-ray structure of one of the two Nb(HFIP)$_6^-$ anions in the asymmetric unit of crystals of [2,6-(CH$_3$)$_2$C$_6$H$_4$N$^+$][Nb(HFIP)$_6^-$] is shown in FIG. 1. The unlabeled shaded circles are fluorine atoms, while the unlabeled large open circles are carbon atoms and unlabeled small open circles are hydrogen atoms. The Nb—O distnaces range from 1.929(8) to 1.998(8)Å.

Experiment 19

Synthesis of [LiTa(HFIP)$_6$]·3(C$_2$H$_5$)$_2$O

A mixture of freshly sublimed TaCl$_5$ (1.51 g, 4.21 mmol) and Li(HFIP) (4.39 g, 25.3 mmol) was dissolved in 40 mL dry Et$_2$O. The initial reaction was sufficiently exothermic to boil the solvent, but the reaction quickly cooled to room temperature. The reaction mixture was stirred for 15 h at 25° C., after which the reaction mixture was concentrated using vacuum evaporation. To the resulting solid was dissolved in 20 mL of dry C$_6$F$_6$. The insoluble LiCl was removed by filtration through a fine frit with a portion of diatomaceous earth to aid in filtration of small particles. The filtrate was concentrated under vacuum to yield 4.64 g of LiTa (HFIP)$_6$·3Et$_2$O as a white microcrystalline solid (78% based on Li(HFIP)).

$^1$H NMR spectrum (benzene-$d_6$:hexafluorobenzene (1:9 v:v)) δ 5.24, 3.45 (quartet, $J_{H-H}$ 7.0 Hz) and 1.08 (triplet, $J_{H-H}$=7.0 Hz).

$^{19}$F NMR (benzene-$d_6$:hexafluorobenzene (1:9 v:v)) δ −74.6.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound comprising an anion of the formula $[M_1(XC(CF_a(R_1)_b)(CF_c(R_2)_d)R_3)_m(R_4)_n]^{-1}$, wherein
   $M_1$ is selected from the group consisting of Al, B, V, Ti, Si, Zr, Ge, Sn, Y, Zn, Ga, Nb, Ta, Bi, P, As, Sc, Hf and Sb;
   each X is independently O, S, or $NR_5R_6$;
   each of $R_1$ and $R_2$ are independently H, halide or $C_1$–$C_4$ alkyl;
   each $R_3$ is independently H, $C_1$–$C_4$ alkyl, or $C_4$–$C_{20}$ aryl;
   each $R_4$ is independently $C_1$–$C_{10}$ alkoxide or $C_4$–$C_{20}$ aryloxide;
   each of $R_5$ and $R_6$ are independently H or $C_1$–$C_{10}$ alkyl;
   each of a and c are independently an integer from 0 to 3;
   a+b=3;
   c+d=3;
   m is an integer from 2 to 8; and
   n is an integer from 0 to 4;
   provided at least one of a or c is not 0 and when $M_1$ is Al and a and c are 3, $R_3$ is not phenyl or p-methylphenyl.

2. The compound of claim 1, wherein $M_1$ is selected from the group consisting of Al, B, V, Ti, Si, Zr, Ge, Sn, Cu, Y, Zn, Ga, Nb, Ta, Bi, P, As, Sc, Hf and Sb.

3. The compound of claim 1, wherein $M_1$ is selected from the group consisting of Al, B, Nb and Ta.

4. The compound of claim 1, wherein a and c are 3.

5. The compound of claim 1, wherein X is O.

6. The compound of claim 1, wherein $R_3$ is selected from the group consisting of H, methyl, trifluoromethyl, p-tert-butylphenyl, and phenyl.

7. The compound of claim 1, wherein m is 2, 4 or 6.

8. The compound of claim 1, wherein n is 1.

9. The compound of claim 1, wherein X is O, a and c are 3.

10. The compound of claim 9, wherein $M_1$ is Al.

11. The compound of claim 10, wherein m=2, n=1, $R_3$ is phenyl, and $R_4$ is o-(dihydroxide)phenyl.

12. The compound of claim 10, wherein m=4, n=0.

13. The compound of claim 12, wherein $R_3$ is H.

14. The compound of claim 12, wherein $R_3$ is methyl.

15. The compound of claim 12, wherein $R_3$ is trifluoromethyl.

16. The compound of claim 12, wherein $R_3$ is p-tert-butylphenyl.

17. The compound of claim 9, wherein $M_1$ is B.

18. The compound of claim 17, wherein m=4, n=0, and $R_3$ is H.

19. The compound of claim 9, wherein $M_1$ is Nb, m=6, n=0 and $R_3$ is H.

20. The compound of claim 9, wherein $M_1$ is Ta, m=6, n=0 and $R_3$ is H.

21. A battery comprising a compound of the formula $M_p[M_1(XC(CF_a(R_1)_b)(CF_c(R_2)_d)R_3)_m(R_4)_n]_k$, wherein M is a metal, phosphonium, ammonium or sulfonium;
$M_1$ is a transition metal, or a Group III, IV or V element;
each X is independently O, S, or $NR_5R_6$;
each of $R_1$ and $R_2$ are independently H, halide or $C_1$–$C_4$ alkyl;
each $R_3$ is independently H, $C_1$–$C_4$ alkyl, or $C_4$–$C_{20}$ aryl;
each $R_4$ is independently $C_1$–$C_{10}$ alkyl, $C_1$–$C_{10}$ alkoxide or $C_4$–$C_{20}$ aryloxide;
each of $R_5$ and $R_6$ are independently H or $C_1$–$C_{10}$ alkyl;
each of a and c are independently an integer from 0 to 3;
a+b=3;
c+d=3;
k and p are 1 or 2;
m is an integer from 2 to 8; and
n is an integer from 0 to 4;
provided at least one of a or c is not 0.

22. The battery of claim 21, wherein p is 1.

23. The battery of claim 22, wherein $M_1$ is selected from the group consisting of Al, B, V, Ti, Si, Zr, Ge, Sn, Cu, Y, Zn, Ga, Nb, Ta, Bi, P, As, Sc, Hf and Sb.

24. The battery of claim 22, wherein $M_1$ is selected from the group consisting of Al, B, Nb and Ta.

25. The battery of claim 22, wherein a and c are 3.

26. The battery of claim 22, wherein X is O.

27. The battery of claim 22, wherein $R_3$ is selected from the group consisting of H, methyl, trifluoromethyl, p-methylphenyl, p-tert-butylphenyl, and phenyl.

28. The battery of claim 22, wherein m is 2, 3, 4 or 6.

29. The battery of claim 22, wherein M is Li and n is 1.

30. The battery of claim 29, wherein $R_4$ is $C_1$–$C_{10}$ alkyl.

31. The battery of claim 29, wherein $R_4$ is selected from the group consisting of methyl and ethyl.

32. The battery of claim 22, wherein X is O, a and c are 3.

33. The battery of claim 32, wherein M is Li and $M_1$ is Al.

34. The battery of claim 33, wherein m=2, n=1, $R_3$ is phenyl, and $R_4$ is a substituted o-(dihydroxide)phenyl.

35. The battery of claim 33, wherein m=2, n=1, $R_3$ is phenyl, and $R_4$ is o-(dihydroxide)phenyl.

36. The battery of claim 33, wherein m=4 and n=0.

37. The battery of claim 36, wherein $R_3$ is H.

38. The battery of claim 36, wherein $R_3$ is methyl.

39. The battery of claim 36, wherein $R_3$ is trifluoromethyl.

40. The battery of claim 36, wherein $R_3$ is p-tert-butylphenyl.

41. The battery of claim 36, wherein $R_3$ is p-methylphenyl.

42. The battery of claim 36, wherein $R_3$ is phenyl.

43. The battery of claim 33, wherein m=3, n=1 and $R_3$ is phenyl.

44. The battery of claim 43, wherein $R_4$ is methyl.

45. The battery of claim 43, wherein $R_4$ is ethyl.

46. The battery of claim 32, wherein M is Li and $M_1$ is B.

47. The battery of claim 46, wherein m=4, n=0, and $R_3$ is H.

48. The battery of claim 32, wherein M is Li and $M_1$ is Nb, m=6, n=0 and $R_3$ is H.

49. The battery of claim 32, wherein M is Li and $M_1$ is Ta, m=6, n=0 and $R_3$ is H.

50. A solid polymer comprising electrolyte of the formula $M_p[M_1(XC(CF_a(R_1)_b)(CF_c(R_2)_d)R_3)_m(R_4)_n]_k$, wherein M is a metal, phosphonium, ammonium or sulfonium;
$M_1$ is a transition metal, or a Group III, IV or V element;
each X is independently O, S, or $NR_5R_6$;

each of $R_1$ and $R_2$ are independently H, halide or $C_1$–$C_4$ alkyl;

each $R_3$ is independently H, $C_1$–$C_4$ alkyl, or $C_4$–$C_{20}$ aryl;

each $R_4$ is independently $C_1$–$C_{10}$ alkyl, $C_1$–$C_{10}$ alkoxide or $C_4$–$C_{20}$ aryloxide;

each of $R_5$ and $R_6$ are independently H or $C_1$–$C_{10}$ alkyl;

each of a and c are independently an integer from 0 to 3;

a+b=3;

c+d=3;

k and p are 1 or 2;

m is an integer from 2 to 8; and n is an integer from 0 to 4;

provided at least one of a or c is not 0.

51. The solid polymer of claim 50, further comprising a polymer selected from the group consisting of polyethylene glycol, polyethylene glycol, polyethylene, polypropylene, polystyrene, polybutadiene; poly(vinyl fluoride), polychloroprene, poly(dimethylsiloxane), poly(vinyl chloride), poly(ethylene imine), poly(propylene oxide), amorphous poly(ethylene oxide), poly(ethylene oxide) and mixtures thereof.

52. An electrochemical device comprising the solid polymer of claim 50.

53. An electrolyte for an electrochemical device comprising a lithium salt of a metal anion comprising at least one polyfluoroalkoxide ligand.

54. The electrolyte of claim 53, wherein said lithium salt has conductivity of at least about 50 $\mu Scm^{-1}$ in THF at about 0.01 M concentration.

55. The electrolyte of claim 53, wherein said lithium salt has conductivity of at least about 50 $\mu Scm^{-1}$ in glyme at about 0.01 M concentration.

56. A compound comprising a mono- or di-anion metal ligand complex having at least two polyfluorinated alkoxide ligands, wherein a lithium salt of said compound has conductivity of at least about 50 $\mu Scm^{-1}$ in THF at about 0.01 M concentration at 25° C.

57. A compound comprising a mono- or di-anion metal ligand complex having at least two polyfluorinated alkoxide ligands, wherein a lithium salt of said compound has conductivity of at least about 50 $\mu Scm^{-1}$ in glyme at about 0.01 M concentration at 25° C.

* * * * *

UNITED STATES PATENT AND TRADEMARK OFFICE
CERTIFICATE OF CORRECTION

PATENT NO. : 6,221,941 B1
DATED : April 24, 2001
INVENTOR(S) : Steven H. Strauss; Benjamin G. Nolan; Thomas J. Barbarich; Juston J. Rockwell It is certified that error appears in the above-identified patent and that said Letters Patent is hereby corrected as shown below:

Title page,
Under the heading, OTHER PUBLICATIONS:

Line 4 reading "nating anions $Al(OCH(CF_3)_2)_4)^-$, and" should read -- nating anions $Al(OCH(CF_3)_2)_4)^-$, $Al(OC(CH_3)(CH_3)_2)_4)^-$, and --; and
the beginning of line 6 reading "Tl" should read -- $Tl^+$ --.

Under the second column:
Line 7, reading "$Na_2Y(OCH(CF_3)_{26}(THF)3$" should read
-- $Na_2Y(OCH(CF_3)_2)_6(THF)_3$ --;
Line 8, reading "$Na_2Y(OCMe(CF_3)_2)_5(THF)3$" should read
-- -- $Na_2Y(OCMe(CF_3)_2)_5(THF)_3$ --;
Lines 10-12, reading "Samuels, et al.; "Structure/Volatility Correlation of Sodium and Zirconium Fluoroalkoxides"; *Chem. Mater. v* 6; 1995; pp. 929-935." should read -- Samuels, et al.; "Chemical Vapor Deposition of Metal Fluorides Using Sodium and Zirconium Fluoroalkoxides"; *Chem Mater. v.* 6; 1994; pp. 1684-1692. --;
Line 26, reading "chem. Soc., vol. 143 1996" should read -- chem. Soc., vol. 143, 1996 --;
Line 42, reading "$Cu(OCH(CF_3)_{24}$" should read -- $Cu(OCH_{(3)}2)_4$ --; and
Line 45-46, reading "*Inorg. Chem. v. 30*; pp. 1969-1970." should read
-- *Inorg. Chem. v. 30*; 1991; pp. 1969-1970. --.

Title page, ABSTRACT,
Line 4, reading "provides a compound comprising a anion" should read -- provides a compound comprising an anion --.

Column 2,
Line 18, reading "(e.g., $CB_6$, $CB_9$, $CB_{11}$)" should read -- (e.g., $CB_5$, $CB_9$, $CB_{11}$) --.

Column 3,
Line 67, reading "$(Et_2O)nH^-$," should read -- $(Et_2O)nH^+$, --.

Column 12,
Line 10, change the "o" in the formula to a subscript.

UNITED STATES PATENT AND TRADEMARK OFFICE
CERTIFICATE OF CORRECTION

PATENT NO. : 6,221,941 B1
DATED : April 24, 2001
INVENTOR(S) : Steven H. Strauss; Benjamin G. Nolan; Thomas J. Barbarich; Juston J. Rockwell It is certified that error appears in the above-identified patent and that said Letters Patent is hereby corrected as shown below:

Column 13,
Line 56, reading "(5.2445 g, 95" should read -- (5.2445 g, 95% --.

Column 14,
Line 24, reading "(0.2082 g, 2069 mmol)" should read -- (0.2082 g, 0.2069 mmol) --.

Column 17,
Line 2, reading "(quartet, $J_{H-H}$ 7.0 Hz)" should read -- (quartet, $J_{H-H}$ = 7.0 Hz) --.

Signed and Sealed this

Twenty-third Day of October, 2001

Attest:

Attesting Officer

NICHOLAS P. GODICI
Acting Director of the United States Patent and Trademark Office

UNITED STATES PATENT AND TRADEMARK OFFICE
CERTIFICATE OF CORRECTION

PATENT NO. : 6,221,941 B1  Page 1 of 1
DATED : April 24, 2001
INVENTOR(S) : Steven H. Strauss; Benjamin G. Nolan; Thomas J. Barbarich; Juston J. Rockwell It is certified that error appears in the above-identified patent and that said Letters Patent is hereby corrected as shown below:

Column 1,
Line 17, insert -- and CHE-9308583 --.

Column 13,
Line 33, "m/z 527.1 [(M-Li)⁻." should read -- m/z 527.1 [(M-Li). --.

Signed and Sealed this

Twenty-fifth Day of December, 2001

Attest:

JAMES E. ROGAN
Attesting Officer    Director of the United States Patent and Trademark Office